United States Patent [19]
Barlozzari et al.

[11] Patent Number: 6,103,698
[45] Date of Patent: Aug. 15, 2000

[54] DOLASTATIN-15 DERIVATIVES IN COMBINATION WITH TAXANES

[75] Inventors: Teresa Barlozzari, Wellesley; Andreas Haupt, Northborough, both of Mass.

[73] Assignee: BASF Aktiengesellschaft, Germany

[21] Appl. No.: 08/819,101

[22] Filed: Mar. 13, 1997

[51] Int. Cl.$^7$ .......................... A61K 38/00; A61K 31/335
[52] U.S. Cl. ................................ 514/18; 514/17; 514/16; 514/449
[58] Field of Search ................................ 514/18, 449, 16, 514/17

[56] References Cited

U.S. PATENT DOCUMENTS

| | | | |
|---|---|---|---|
| 4,816,444 | 3/1989 | Pettit et al. | 514/17 |
| 4,879,278 | 11/1989 | Pettit et al. | 514/17 |
| 5,227,400 | 7/1993 | Holton et al. | 514/444 |
| 5,248,796 | 9/1993 | Chen et al. | 549/510 |
| 5,250,683 | 10/1993 | Holton et al. | 544/60 |
| 5,254,580 | 10/1993 | Chen et al. | 514/449 |
| 5,272,171 | 12/1993 | Ueda et al. | 514/449 |
| 5,278,324 | 1/1994 | Kingston et al. | 549/510 |
| 5,447,936 | 9/1995 | Hausheer et al. | 514/283 |
| 5,484,612 | 1/1996 | Brown | 424/649 |
| 5,494,930 | 2/1996 | Shimizu et al. | 514/450 |
| 5,502,032 | 3/1996 | Haupt et al. | 514/17 |
| 5,504,191 | 4/1996 | Pettit et al. | 530/330 |
| 5,525,613 | 6/1996 | Wynn et al. | 514/304 |
| 5,530,097 | 6/1996 | Pettit et al. | 530/330 |
| 5,543,423 | 8/1996 | Zelle et al. | 514/332 |
| 5,565,478 | 10/1996 | Kohn et al. | 514/359 |

FOREIGN PATENT DOCUMENTS

| | | |
|---|---|---|
| 2 697 752 | 5/1994 | France . |
| WO93/18210 | 9/1993 | WIPO . |
| WO94/10995 | 5/1994 | WIPO . |
| WO 96/40751 | 12/1996 | WIPO . |
| WO 96/40752 | 12/1996 | WIPO . |

OTHER PUBLICATIONS

Conlon, D. et al., "In vivo antitumor activity of LU103793 in combination with Taxol," *J. of Cancer Research,* 38:320 (Mar. 21, 1997). (From Proceedings of the American Association for Cancer Research Annual Meeting, 1997, Abstract No. 2142).

Leopold, W. et al., "Therapeutic Synergy of Trimetrexate (C1–898) in Combination With Doxorubicin, Vincristine, Cytoxan, 6–Thioguanine, Cisplatin, or 5–Fluorouracil Against Intraperitoneally Implanted P388 Leukemia," *NCI Monographs,* (5): 99–104 (1987).

Schabel, Jr., F.M. et al., "Quantitative Evaluation of Anticancer Agent Activity in Experimental Animals," *Pharmac Ther. A.,* 1: 411–435 (1977).

Chou, T.–C. et al., "Computerized Quantitation of Synergism and Antagonism of Taxol, Topotecan, and Cisplatin Against Human Teratocarcinoma Cell Growth" a Rational Approach to Clinical Protocol Design, *J. of the National Cancer Institute,* 86 (20): 1517–1524 (1994).

Knick, V.C. et al., "Vinorelbine Tartrate and Paclitaxel Combinations: Enhanced Activity Against In Vivo P388 Murine Leukemia Cells," *J. of the National Cancer Institute,* 87 (14): 1072–1077 (1995).

Bissery, M.C. et al., "Docetaxel in combination with vinorelbine: Preclinical–clinical correlation," *Proc. Am. Soc. Clin. Oncol. 15 32 Meet,* 487 (1996) Abstract 96–43670.

Beckwith, M. et al., "Growth Inhibition of Human Lymphoma Cell Lines by the Marine Products, Dolastatins 10 and 15," *J. Nat'l. Cancer Inst.,* 85: 483–488 (1993).

Freidinger, R. et al., "Protected Lactam–Bridged Dipeptides for Use as Conformational Constraints in Peptides," *J. Org. Chem.:* 104–109 (1982).

Galeotti, N. et al., "Formation of Oxazolines and Thiazolines in Peptides by the Mitsunobu Reaction," *Tetrahedron Letters,* 33(20): 2807–2810 (1992).

Wipf, P. et al., "A Short, Stereospecific Synthesis of Dihydrooxazoles from Serine and Threonine Derivatives," *Tetrahedron Letters,* pp. 907–910 (1992).

Tully, W. R. et al., "2–(Oxadiazolyl)– and 2–(Thiazolyl)imidazo[1,2–a]pyrimidines as Agonists and Inverse Agonists at Benzodiazepine Receptors," *J. Med. Chem.,* 34: 2060–2067 (1991).

Miyazaki, K. et al., "Synthesis and Antitumor Activity of Novel Dolastatin–10 Analogs," *Chem. Pharm. Bull.,* 43(10): 1706–1718 (1995).

Pettit, G. R. et al., "The Isolation and Structure of a Remarkable Marine Animal Antineoplastic Constituent: Dolastatin 10", *J. Am. Chem. Soc.,* 109: 6883–6885 (1987).

Pettit, G. R. et al., "Antineoplastic Agents 337. Synthesis of Dolastatin–10 Structural Modifications," *Anti–Cancer Drug Design,* 10: 529–544 (1995).

Pettit, G. R et al., "Antineoplastic Agents. 220. Synthesis of Natural (–)–Dolastatin 15", *J. Am. Chem. Soc.,* 113: 6692–6693 (1991).

Bai, R. et al., "Dolastatin 15, a potent antimitotic depsipeptide derived from *Dolabella auricularia.* Interaction with tubulin and effects on cellular microtubules", *1–Pharmacology, Abstract 117:*103735g p. 41 (1992).

Pettit, G. R. et al., "Isolation and Structure of the Cytostatic Depsipeptide Dolastatin 13 from the Sea Hare *Dolabella auricularia,*" *J. Am. Chem. Soc.,* 111 (13): 5015–5017 (1989).

(List continued on next page.)

*Primary Examiner*—Jerome D. Goldberg
*Attorney, Agent, or Firm*—Hamilton, Brook, Smith & Reynolds, P.C.

[57] ABSTRACT

The present invention provides compositions and methods for the treatment of cancer in a subject wherein compounds of Formula I as defined herein in combination with paclitaxel, taxotere or modified taxane or taxoid analogs provide enhanced anticancer effects over the effects achieved with the individual compounds.

25 Claims, 4 Drawing Sheets

OTHER PUBLICATIONS

Schmidt, U. et al., "Amino Acids and Peptides; 59. Synthesis of Biologically Active Cyclopeptides; 9. Synthesis of 16 Isomers of Dolastatin 3; I. Synthesis of the 2–(1–aminoalkyl)–thiazole–4–carboxylic Acids", *Synthesis:* 233–236 (Mar. 1987).

Pettit, G. R. et al., "Isolation and Structure of the Cytostatic Linear Depsipeptide Dolastatin 15", *J. Org. Chem.,* 54: 6005–6006 (1989).

Rose, W.C., "Taxol–Based Combination Chemotherapy and Other In Vivo Preclinical Antitumor Studies", *J. of the National Cancer Institute Monographs (15):* 47–53 (1993).

Holton, R. A. et al., "First Total Synthesis of Taxol. 1. Functionalization of the B Ring," *J. Am. Chem. Soc.,* 116: 1597–1601 (1994).

Nicolaou, K. C. et al., "Total Synthesis of Taxol," *Nature,* 367: 630–634 (1994).

Kumar, N., "Taxol–induced Polymerization of Purified Tubulin," *J. Biol. Chem.* 256: 10435–10441 (1981).

Rowinsky, E. K. et al., "Taxol: A Novel Investigational Antimicrotubule Agent," *J. Nat'l Cancer Inst.,* 82: 1247–1259 (1990).

Schiff, P. B. et al., "Promotion of Microtubule Assembly in vitro by taxol," *Nature,* 277: 665–667 (1979).

McGuire, W. P. et al., "Taxol: A Unique Antineoplastic Agent with Significant Activity in Advanced Ovarian Epithelial Neoplasms," *Ann. Int. Med.,* 111: 273–279 (1989).

Holmes, F. et al., "Phase II Trial of Taxol, an Active Drug in the Treatment of Metastatic Breast Cancer," *J. Nat'l Cancer Inst.,* 83: 1797–1805 (1991).

Kohn, E. et al., "A Pilot Study of Taxol, Cisplatin, Cyclophosphamide, and G–CSF In Newly Diagnosed Stage III/IV Ovarian Cancer Patients," *Am. Society for Clinical Oncology,* 12: Abstract 814 (1993).

Bai, R. et al., "Structure–Activity Studies with Chiral Isomers and with Segments of the Antimitotic Marine Peptide Dolastatin 10," *Biochem. Pharmacology,* 40: 1859–1864 (1990).

Kohn, E. C. et al., "Dose–Intense Taxol: High Response Rate in Patients With Platinum–Resistant Recurrent Ovarian Cancer," *J. Nat'l Cancer Inst.,* 86:18–24 (1994). Abstract *814.

(i)

(ii)

(iii)

(iv)

(v)

(vi)

(vii)

(viii)

(ix)

(x)

(xi)

(xii)

(xiii)

(xiv)

(xv)

(xvi)

(xvii)

```
                          SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:1:

Xaa Val Xaa Pro Xaa
1               5

(2) INFORMATION FOR SEQ ID NO:2:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:2:

Xaa Xaa Xaa Pro Xaa
1               5

(2) INFORMATION FOR SEQ ID NO:3:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:3:

Xaa Val Xaa Pro Pro Xaa
1               5
```

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Xaa Xaa Xaa Pro Xaa
1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Xaa Ile Xaa Pro Xaa
1               5

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Xaa Val Xaa Pro Pro Val Phe
1               5

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Xaa Val Xaa Pro Xaa Val Phe
1               5

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Xaa Ile Xaa Pro Pro Val Phe 1               5

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Xaa Leu Xaa Pro Pro Val Phe
1               5

(2) INFORMATION FOR SEQ ID NO:10:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Xaa Val Xaa Pro Pro Phe Phe
1               5

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Xaa Val Xaa Pro Pro Val
1               5

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Xaa Val Xaa Pro Pro
1               5

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

```
Xaa Val Xaa Xaa
1
```

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

```
Xaa Xaa Xaa Pro Pro
1               5
```

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

```
Xaa Val Xaa Pro Pro Xaa Phe
1               5
```

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

```
Xaa Val Xaa Pro Pro Leu Phe
1               5
```

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

```
Xaa Val Xaa Pro Pro Ile Phe
1               5
```

DOLASTATIN-15 DERIVATIVES IN COMBINATION WITH TAXANES

BACKGROUND OF THE INVENTION

Cancer is a disease for which many potentially effective treatments are available. However, due to the prevalence of cancers of various types and the serious effects it can have, more effective treatments, especially those with fewer adverse side effects than currently available forms of treatment, are needed.

SUMMARY OF THE INVENTION

This invention relates to pharmaceutical compositions useful in treating cancer in a mammal. The pharmaceutical compositions of the present invention comprise two compounds: a first compound which is paclitaxel, taxotere or a modified taxane or taxoid analog and a second compound, which is a compound of Formula I:

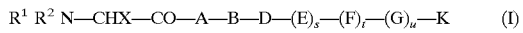

Formula I is discussed in detail below. Some examples of compounds of Formula I are specifically presented herein. For example, compounds of Formula I can be those in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tert-butylglycyl; D is thiazolidinylcarbonyl, 3,4-dehydroprolyl or prolyl; E is prolyl, thiazolidinyl-4-carbonyl, homoprolyl, hydroxyprolyl or 3,4-dehydroprolyl; and K is a substituted amino moiety having the formula $R^5$—N—$R^6$, wherein $R^5$ is hydrogen or $C_1$–$C_4$-alkoxy and $R^6$ is a monovalent radical such as (1)- or (2)-adamantyl; $(CH_2)v$-phenyl with v=1; α,αdimethylbenzyl; a $C_1$–$C_{12}$ linear or branched hydroxyalkyl group, such as —$C(CH_3)_2$—$CH_2$—$CH_2$—OH, also referred to as 3-hydroxy-1,1-dimethylpropyl; a $C_3$–$C_{10}$ cycloalkyl group, such as bicyclo [3.3.0]octa-1-yl, 1-methylcyclopentyl or 1-methylcyclohexyl; or a $C_1$–$C_{12}$ linear or branched alkyl group, such as —$C(CH_3)_3$, also referred to as tert-butyl;

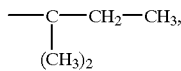

also referred to as 1,1-dimethylpropyl;

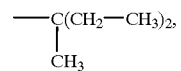

also referred to as 1-methyl-1-ethylpropyl;

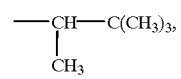

also referred to as (S)— or (R)—1-methyl-2,2dimethylpropyl;

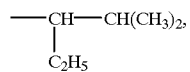

also referred to as (S)— or (R)—1-ethyl-2methylpropyl;

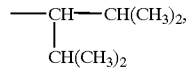

also referred to as 1-isopropyl-2-methylpropyl; or —$C(CH_3)_2$—$CH(CH_3)_2$, also referred to as 1,1-dimethyl-2-methylpropyl;
—$CH(CH_3)_2$, also referred to as isopropyl;
—$CH(CH_3)CH_2CH_3$, sec-butyl [(S) or (R)]; or
—$CH(CH_3)CH(CH_3)_2$, also referred to as 1,2-dimethylpropyl.

Each compound is present in the pharmaceutical composition in an effective amount. The pharmaceutical composition can include one or more of each type of compound (e.g., one or more of the first type of compound, such as paclitaxel or paclitaxel and taxotere and one or more compounds of Formula I).

This invention also relates to methods of treating cancer in a mammal in which the pharmaceutical compounds described herein are used. In the method of the present invention, the two compounds are administered in the pharmaceutical composition or as individual/separate compounds which are given sufficiently close in time to have the desired effect.

It has been discovered that, surprisingly the combination of paclitaxel, taxotere or a modified taxane or taxoid analog as described herein and a compound having Formula I as described herein provides enhanced or therapeutically synergistic anticancer effects in vivo. For purposes of this invention, two drugs are considered therapeutically synergistic if a combination regimen produces a significantly better tumor cell kill than the best constituent when it is administered alone at optimal or maximum tolerated doses. Differences in tumor cell kill less than half a decade are not considered signficant.

DETAILED DESCRIPTION OF THE INVENTION

Figure 1A:
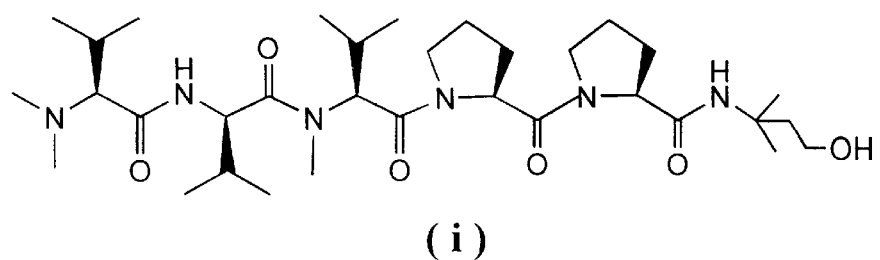
FIGS. 1A–1D depict compounds i–xvii, as examples of compounds of Formula I.
Figure 1A:
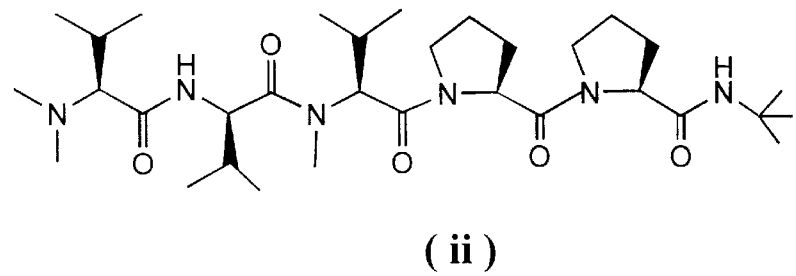
Figure 1A:
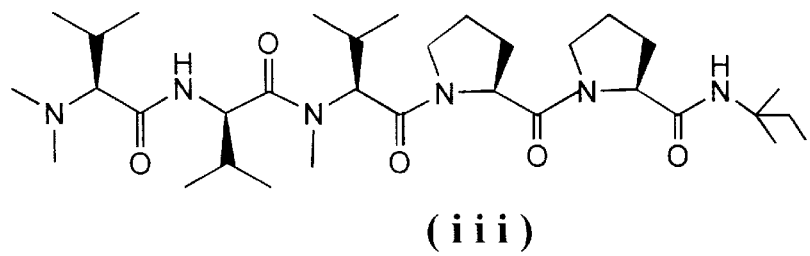
Figure 1A:
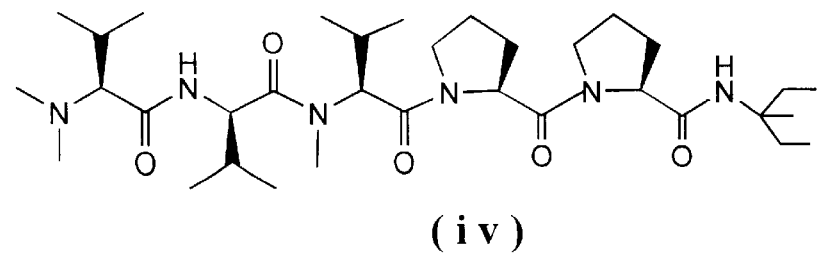
Figure 1B:
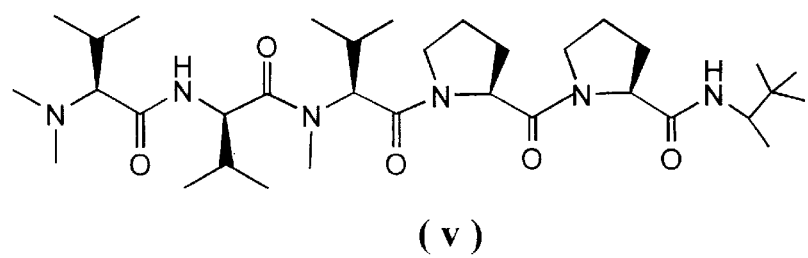
Figure 1B:
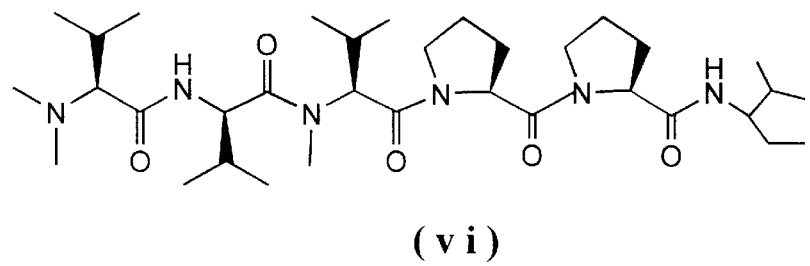
Figure 1B:
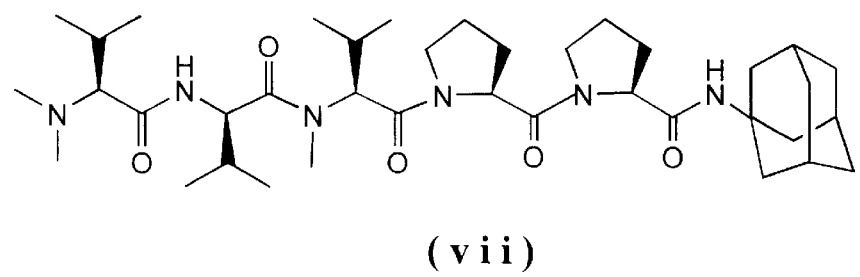
Figure 1B:
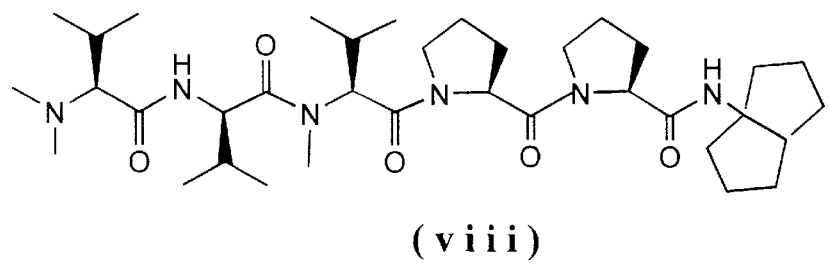
Figure 1C:
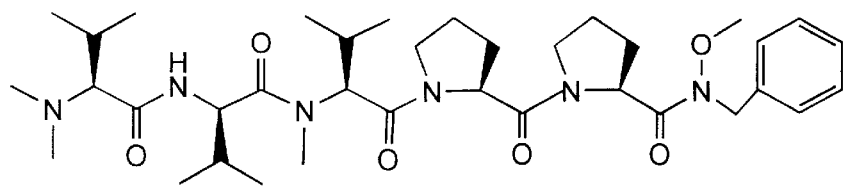
Figure 1C:
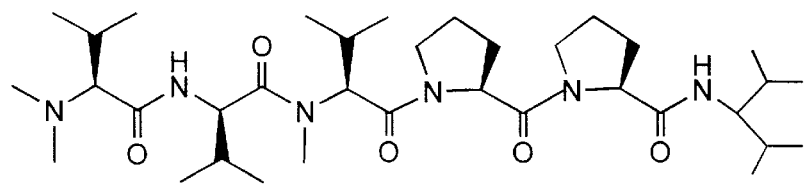
Figure 1C:
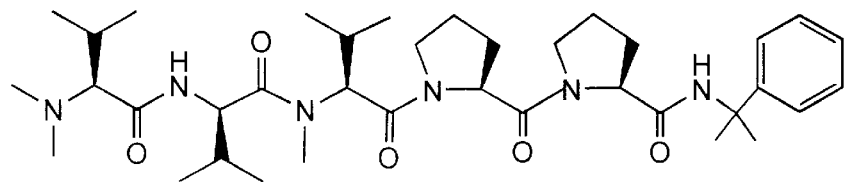
Figure 1C:
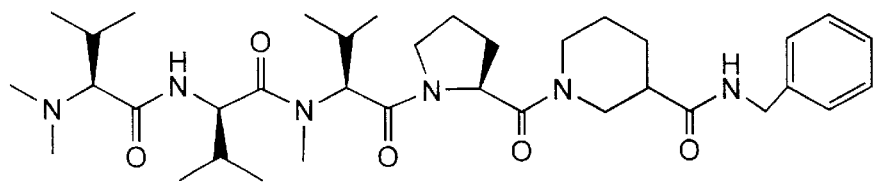

The present invention relates to pharmaceutical compositions useful in treating cancer in a mammal. The pharmaceutical composition of the present invention comprises two compounds: a first compound which is paclitaxel, taxotere or a modified taxane or taxoid analog and a second compound of Formula I as further described below. Each compound is present in the pharmacuetical composition in an effective amount. One or more of each type of compound can be present in the pharmaceutical composition or administered in the present method. As used herein the term "an effective amount" refers to an amount sufficient to elicit the desired biological response. In the instant invention, the desired biological response is inhibition (partial or total) of formation of a tumor or a hematological malignancy, reversal of the development of a solid tumor or other malignancy or prevention or reduction of its further progression.

Paclitaxel, Taxotere or a Modified Taxane or Taxoid Analog

Paclitaxel (Taxol®), which is one example of a first compound of the pharmaceutical composition, is a diterpene isolated from the bark of the Western (Pacific) yew, *Taxus brevifolia* and is representative of a class of therapeutic agent having a taxane ring system. The formula for paclitaxel is:

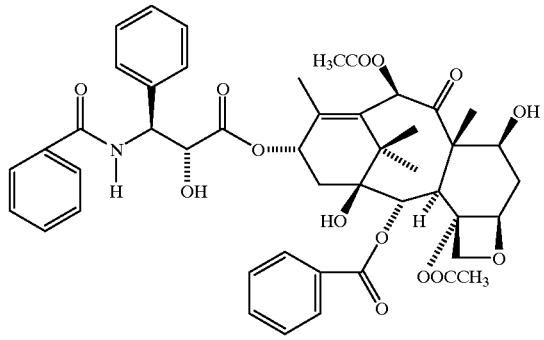

Paclitaxel and its analogs have been produced by partial synthesis from 10-deacetylbaccatin III, a precursor obtained from yew needles and twigs, and by total synthesis. See Holton, et al., *J. Am. Chem. Soc.* 116:1597–1601 (1994) and Nicolaou, et al., *Nature* 367:630 (1994). Paclitaxel has been demonstrated to possess antineoplastic activity. More recently, it was shown that the antitumor activity of paclitaxel is due to a promotion of microtubule polymerization. See Kumar, N., *J. Biol. Chem.* 256:10435–10441 (1981); Rowinsky, et al., *J. Natl. Cancer Inst.* 82:1247–1259 (1990); and Schiff, et al., *Nature* 277:655–667 (1979). Paclitaxel has now demonstrated efficacy in several human tumors in clinical trials. See McGuire, et al., *Ann. Int. Med.* 111:237–279 (1989); Holmes, et al., *J. Natl. Cancer Inst.* 83:1797–1805 (1991); Kohn et al., *J. Natl. Cancer Inst.* 86:18–24 (1994); and Kohn, et al., *American Society for Clinical Oncology* 12 (1993). Paclitaxel is available from Bristol-Myers Squibb Company, New York, N.Y. by the registered tradename Taxol®.

The first compound in the pharmaceutical composition is typically paclitaxel (Taxol®), taxotere or a modified taxane or taxoid analog. The modified taxane or taxoid analogs are those compounds having a taxane ring bearing modified side chains. A number of these analogs have improved properties, such as greater water solubility and stability than that of naturally occurring paclitaxel. For example, RPR109881 is a new oral and iv active taxoid analog under development by Rhone-Poulenc Rhorer and currently in Phase I Clinical Trials. These analogs are known to those of skill in the art and are disclosed, for example, in U.S. Pat. Nos. 5,278,324; 5,272,171; 5,254,580; 5,250,683; 5,248,796; and 5,227,400, the disclosures of which are incorporated herein by reference. Taxotere can be prepared by the method in WO 93/18210, the disclosure of which is incorporated herein by reference. In particular embodiments, the first compound in the pharmaceutical composition is paclitaxel or taxotere.

Compounds of Formula I

A number of short peptides with significant activity as inhibitors of cell growth have been isolated from the Indian Ocean sea hare *Dolabella auricularia* (Bai, et al., *Biochem. Pharmacology*, 40: 1859–1864 (1990); Beckwith et al., *J. Natl. Cancer Inst.*, 85: 483–488 (1993) and references cited therein). These include Dolastatins 1–10 (U.S. Pat. No. 4,816,444, issued to Pettit et al.) and Dolastatin-15 (European Patent Application No. 398558). Dolastatin-15, for example, markedly inhibits the growth of the National Cancer Institute's P388 lymphocytic leukemia cell line, a strong predictor of efficacy against various types of human malignancies. This compound, however, is present only in trace quantities in the sea hare and is difficult to isolate, expensive to synthesize and suffers from poor aqueous solubility.

The compounds of Formula I are derivatives of Dolastatin-15, which overcome the above-mentioned disadvantages of Dolastatin-15 while retaining antineoplastic activity or exhibiting greater antineoplastic activity than the natural product. The Dolastatin-15 derivatives of Formula I, which are employed in combination with paclitaxel, taxotere or a modified taxane or taxoid analog in the present invention, can be synthesized, as described herein and in related copending application U.S. Ser. No. 08/472,453, filed Jun. 7, 1995, the teachings of which are incorporated herein in their entirety.

The Dolastatin-15 derivatives of Formula I generally comprise L-amino acids, but they can also contain one or more D-amino acids, as described in related copending application U.S. Ser. No. 08/472,453 filed on Jun. 7, 1995. The compounds of Formula I can also be present as salts with physiologically-compatible acids, such as, but not limited to, hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

For purposes of the present invention, the term "monovalent radical" is intended to mean an electrically neutral molecular fragment capable of forming one covalent bond with a second neutral molecular fragment. Monovalent radicals include the hydrogen atom, alkyl groups (e.g. methyl, ethyl, propyl and tert-butyl groups), cycloalkyl groups, hydroxy alkyl groups, adamantyl groups, halogen atoms (e.g. fluorine, chlorine and bromine atoms), aryl groups (e.g. phenyl, benzyl and naphthyl groups) and alkoxy groups (e.g. methoxy and ethoxy groups). Two monovalent radicals on adjacent sigma-bonded atoms can also form a pi bond between the adjacent atoms. Two monovalent radicals may also be linked together, for example, by a polymethylene unit to form a cyclic structure. For example, the unit —N(R)R', wherein R and R' are monovalent radicals, can, together with the nitrogen atom, form a heterocyclic ring. In addition, two monovalent radicals bonded to the same atom can also form a divalent radical, such as an alkylidene group, for example, a propylidene group, or an oxygen atom.

More specifically, for the compounds of Formula I:

$R^1$ is alkyl, such as $C_1$–$C_3$; cycloalkyl, such as cyclopropyl; alkylsulfonyl, such as $C_1$–$C_3$; fluoroalkyl, such as fluoroethyl, difluoroethyl, fluoroisopropyl; aminosulfonyl which may be substituted by alkyl, such as methyl;

$R^2$ is hydrogen; alkyl, such as $C_1$–$C_3$; fluoroalkyl, such as fluoroethyl, difluoroethyl, fluoroisopropyl; cycloalkyl, such as cyclopropyl;

$R^1$—N—$R^2$ together may be a pyrrolidino or piperidino residue;

A is a valyl, isoleucyl, leucyl, allo-isoleucyl, 2,2-dimethylglycyl, 2-cyclopropylglycyl, 2-cyclopentylglycyl, 3-tert-butylalanyl, 2-tert-butylglycyl, 3-cyclohexylalanyl, 2-ethylglycyl, 2-cyclohexylglycyl, norleucyl or norvalyl residue;

B is a N-alkyl-valyl, -norvalyl, -leucyl, -isoleucyl, -2-tert-butylglycyl, -3-tert-butylalanyl, -2-ethylglycyl, -2-cyclopropylglycyl, -2-cyclopentylglycyl, norleucyl or -2-cyclohexylglycyl residue where N-alkyl is preferably N-methyl or N-ethyl;

D is a prolyl, homoprolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;

E is a prolyl, homoprolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;

F and G are independently selected from the group consisting of prolyl, homoprolyl, hydroxyprolyl, thiazolidinyl-4-carbonyl, 1-aminopentyl-1-carbonyl, valyl, 2-tert-butylglycyl, isoleucyl, leucyl, 3-cyclohexylalanyl, phenylalanyl, N-methylphenylalanyl, tetrahydrosioquinolyl-2-histidyl, 1-aminoindyl-1-carbonyl, 3-pyridylalanyl, 2-cyclohexylglycyl, norleucyl, norvalyl, neopentylglycyl, trytophanyl, glycyl, 2,2-dimethylglycyl alanyl, β-alanyl and 3-naphthylalanyl residues;

X is hydrogen, alkyl (such as $C_1$–$C_5$), cycloalkyl (such as $C_3$–$C_7$), —$CH_2$-cyclohexyl or arylalkyl (such as benzyl or phenethyl);

s, t and u are independently 0 or 1; and

K is hydroxy, alkoxy (such as $C_1$–$C_4$), phenoxy, benzyloxy or a substituted or unsubstituted amino moiety.

In addition, the compounds of Formula I can be present as a salt thereof with physiologically tolerated acids. One subclass of compounds of this invention includes compounds of Formula I wherein $R^1$—N—$R^2$ is a pyrrolidinyl or piperidinyl residue.

Another subclass of compounds of this invention includes compounds of Formula I wherein K is an amino moiety of the formula $R^5$—N—$R^6$, wherein:

$R^5$ is hydrogen, or hydroxy, or $C_{1-7}$ alkoxy, or benzyloxy, or phenyloxy or $C_{1-12}$ linear or branched hydroxyalkyl, such as 3-hydroxy-1,1-dimethylpropyl, or $C_{1-7}$ linear or branched alkyl (which may be substituted by one or more fluoro atoms), or $C_{3-10}$-cycloalkyl, such as, bicyclo [3.3.0] octa-1yl, 1-methylcyclopentyl or 1-methylcylcohexyl; or benzyl (which may be substituted by up to three substituents which may independently be $CF_3$, nitro, $C_{1-7}$ alkylsulfonyl, $C_{1-4}$ alkoxy, phenoxy, benzoxy, halogen, $C_{1-4}$-alkyl, cyano, hydroxy, $N(CH_3)_2$, COOMe, COOEt, COOiPr, or $COONH_2$);

$R^6$ is hydrogen, or $C_{1-12}$ linear or branched alkyl (which may be substituted by one or more fluoro atoms), or $C_{1-12}$ linear or branched hydroxyalkyl, such as 3-hydroxy-1,1-dimethylpropyl, or $C_{3-10}$-cycloalkyl, such as bicyclo [3.3.0] octa-1-yl, or 1-methylcyclopentyl or 1-methylcyclohexyl; or —$(CH_2)_v$—$C_{3-7}$-cycloalkyl (v=0,1,2, or 3), or norephedryl, or norpseudoephedryl, or quinolyl, or pyrazyl, or —$CH_2$-benzimidazolyl, or (1)-adamantyl, or (2)-adamantyl-—$CH_2$-adamantyl, or alpha-methyl-benzyl, or alpha-dimethylbenzyl, or —$(CH_2)v$-phenyl (v=0,1,2, or 3; which may be substituted by up to two substituents which may independently be $CF_3$, nitro, $C_{1-7}$ alkylsulfonyl, $C_{1-4}$ alkoxy, phenoxy, benzoxy, halogen, $C_{1-4}$-alkyl which may form a cyclic system, cyano, hydroxy, $N(CH_3)_2$, COOMe, COOEt, COOiPr, or $COONH_2$), or —$(CH_2)_m$-naphthyl (m=0 or 1); or —$(CH_2)_w$-benzhydryl (w=0,1, or 2); or biphenyl or picolyl or benzothiazolyl or benzoisothiazolyl or benzopyrazolyl or benzoxazolyl or —$(CH_2)_m$-fluorenyl (m=0 or 1); or pyrimidyl or —$(CH_2)_m$-indanyl (m=0 or 1); or —$(CH_2CH_2O)_y$—$CH_3$ (y=0,1,2,3,4, or 5), or —$(CH_2CH_2O)_y$—$CH_2CH_3$ (y=0,1,2,3,4, or 5), or NH—$C_6H_5$ (which may be substituted by up to two substituents which may inde- pendently be $CF_3$, nitro, $C_{1-7}$ alkylsulfonyl, $C_{1-4}$ alkoxy, halogen, $C_{1-4}$ alkyl which may form a cyclic system, cyano, hydroxy, COOMe, COOEt, COOiPr, or $COONH_2$), or —$NCH_3$—$C_6H_5$ or —NH—$CH_2$—$C_6H_5$ or —$NCH_3$—$CH_2$—$C_6H_5$ or 5-membered heteroaryl which may be substituted by up to two substituents which may independently be $CF_3$, nitro, thiomethyl, thioethyl, $C_{3-6}$-cycloalkyl, —$CH_2$—COOEt, $C_{3-4}$-alkylene group forming a bicyclic system with the heterocycle, phenyl; or —$CHR^7$-5-membered heteroaryl (which may be substituted by up to two substituents which may independently be $CF_3$, nitro, cyano, halogen, COOMe, COOEt, COOiPr, $CONH_2$, $C_{1-4}$-alkyl, $C_{1-4}$-alkoxy, phenyl, benzyl, naphthyl, or $C_{1-7}$-alkylsulfonyl [$R^7$=hydrogen, linear or branched $C_{1-5}$ alkyl, benzyl; or $R^7$ and $R^5$ together form a group —$(CH_2)_3$— or —$(CH_2)_4$—).

This subclass includes compounds of Formula I wherein s, t and u are independently 0 or 1; $R^1$, $R^2$ and X are lower alkyl, A is a lower alkyl amino acid, B is a N-loweralkylated lower alkyl amino acid; D,E,F,G and K are as previously defined. With the foregoing in mind, three sets of such compounds can thus be depicted by the following formulas II, III, and IV:

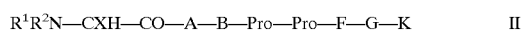

$R^1R^2N$—CXH—CO—A—B—Pro—Pro—F—G—K    II

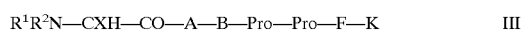

$R^1R^2N$—CXH—CO—A—B—Pro—Pro—F—K    III

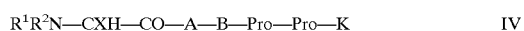

$R^1R^2N$—CXH—CO—A—B—Pro—Pro—K    IV

—$CHR^7$-5-membered heteroaryl may, for example, be represented by one of the following residues:

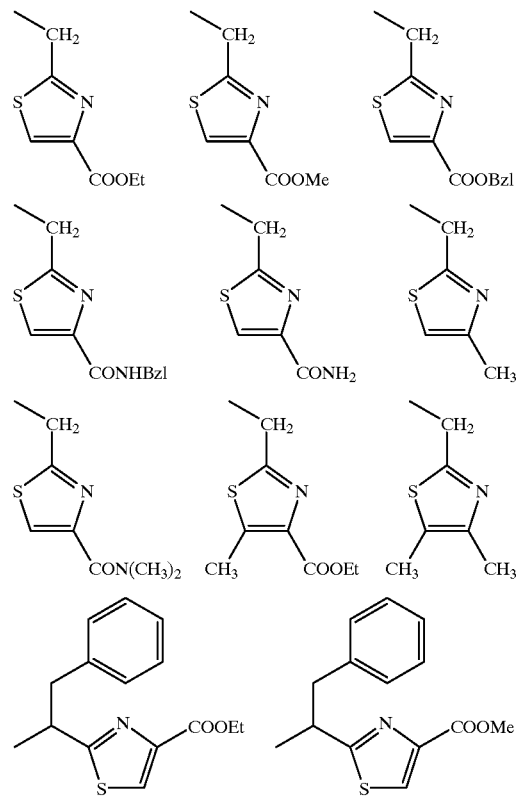

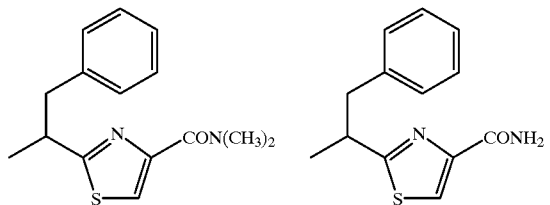
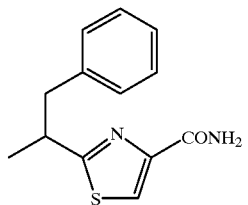
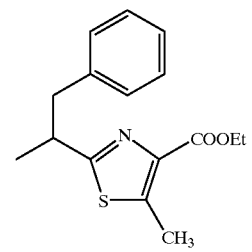
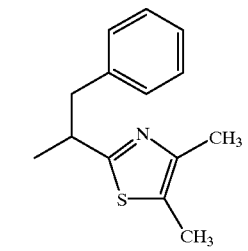
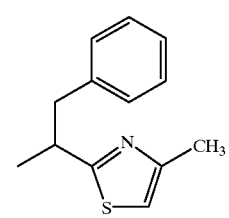
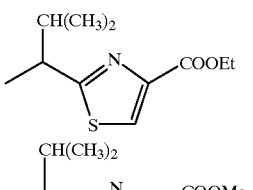
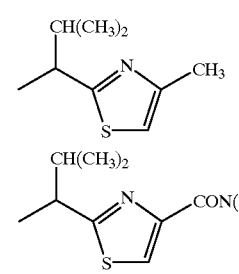
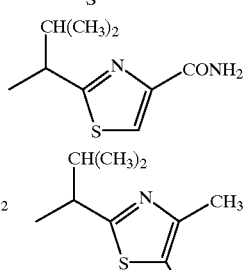
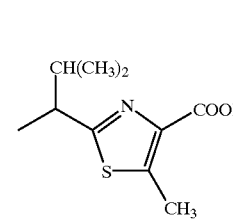
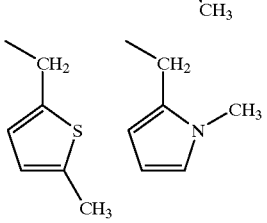
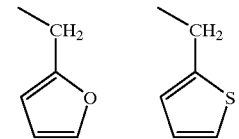
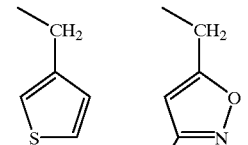
—NR$^5$CHR$^7$-5-membered heteroaryl may, for example, be represented by the following residues:
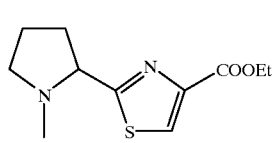
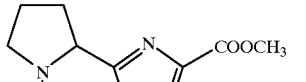
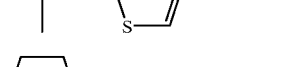
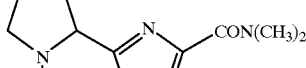
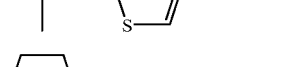
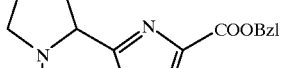
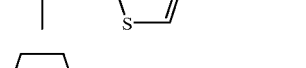
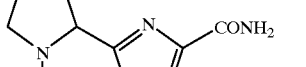
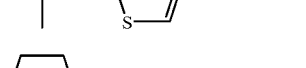
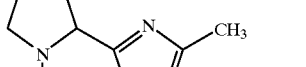
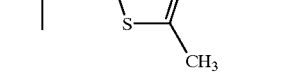
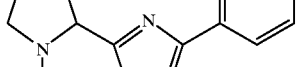
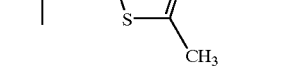
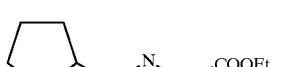
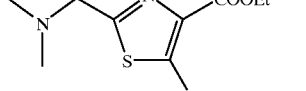
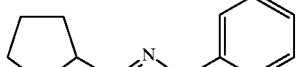
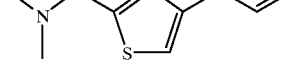
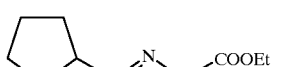
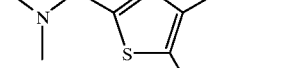
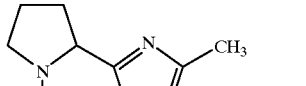
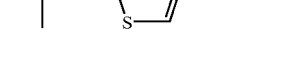
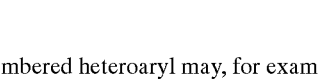
5-membered heteroaryl may, for example, be represented by the following residues:

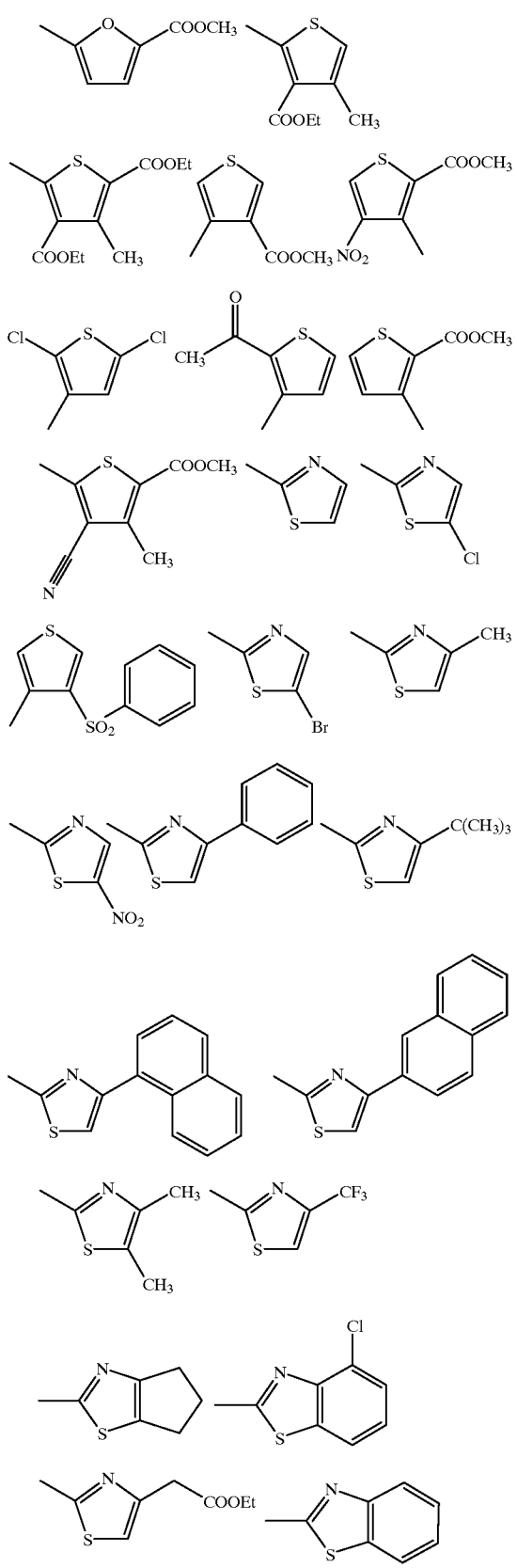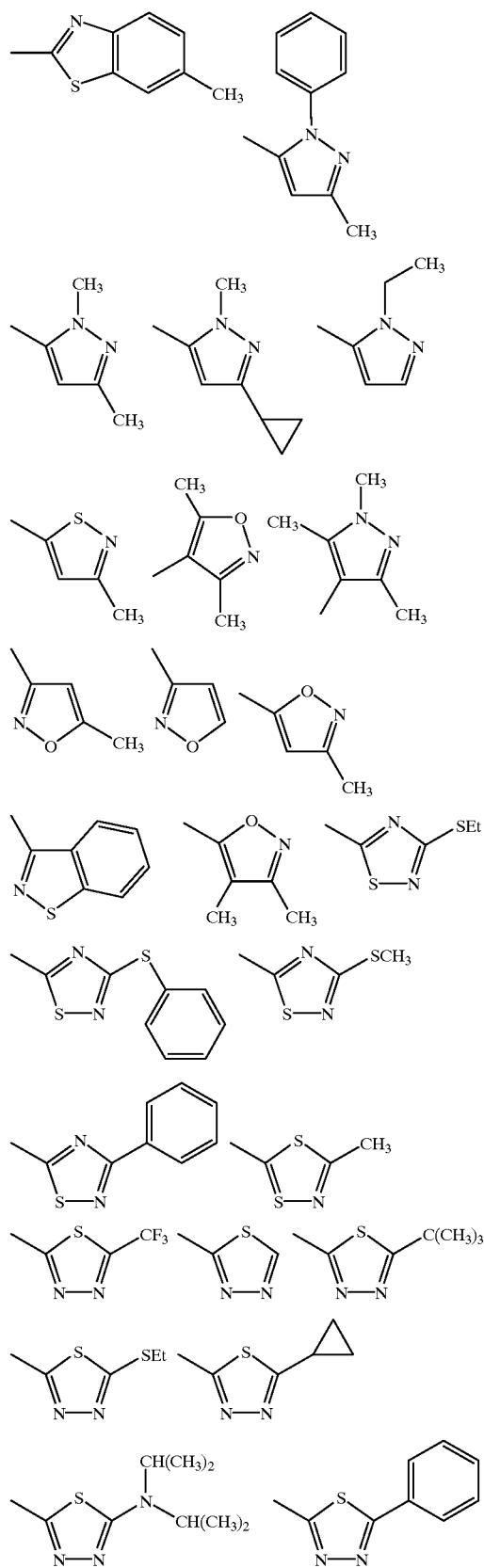

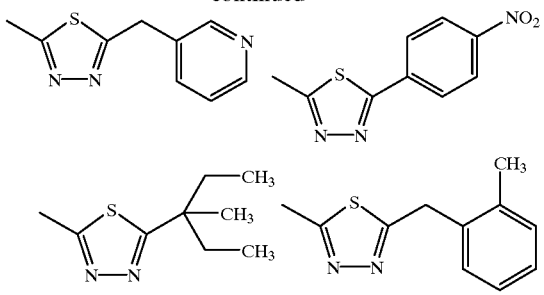

In another subclass of compounds of this invention $R^5$—N—$R^6$ together may form structures selected from the group consisting of:

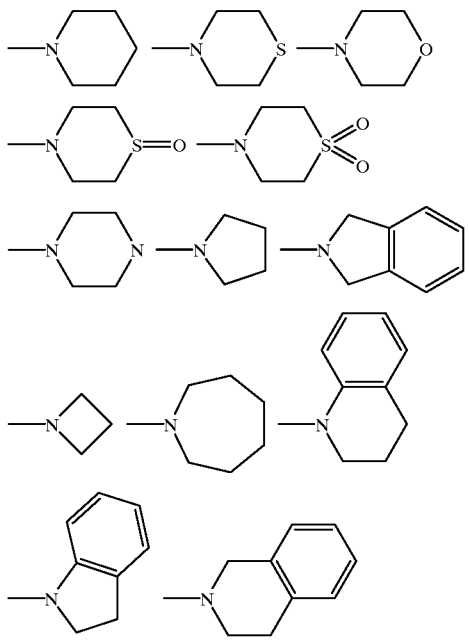

Still another subclass of compounds of this invention includes, for example, compounds of Formula I wherein s, t and u are 1 and K is a hydroxy, alkoxy, phenoxy or benzyloxy moiety.

Yet another subclass of compounds of this invention includes, for example, compounds of Formula I wherein s and t are 1, u is 0 and K is a hydroxy, alkoxy, phenoxy or benzyloxy moiety.

Another subclass of compounds of this invention includes, for example, compounds of Formula I wherein s is 1, t and u are 0 and K is a hydroxy, alkoxy, phenoxy or benzyloxy moiety.

In particular embodiments, the second compound in the pharmaceutical composition of the invention is a compound of Formula I in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or -2-tert-butylglycyl; D is prolyl, thiazolidinyl-4-carbonyl or 3,4 dehydroprolyl; E is prolyl, thiazolidinyl-4-carbonyl, homoprolyl, 3,4-dehydroprolyl or hydroxyprolyl; and K is a substituted or unsubstituted amino moiety having the formula $R^5$—N—$R^6$.

In a further embodiment, the second compound in the pharmaceutical composition is a compound of Formula I in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tertbutylglycyl; D is prolyl, thiazolidinyl-4-carbonyl, or 3,4-dehydroprolyl; E is prolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$–$C_4$ alkoxy and $R^6$ is a $C_1$–$C_{12}$ linear or branched alkyl group or a $C_1$–$C_{12}$ linear or branched hydroxyalkyl group represented, for example, by the following monovalent radicals:

—$C(CH_3)_2$—$CH_2$—$CH_2$—OH, also referred to as 3-hydroxy-1,1-dimethylpropyl;

—$C(CH_3)_3$, also referred to as tert-butyl;

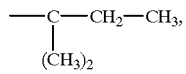

also referred to as 1,1-dimethyl propyl;

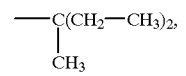

also referred to as 1-methyl-1-ethyl propyl;

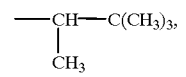

also referred to as (S)— or (R)—1-methyl-2,2-dimethyl propyl;

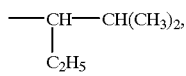

also referred to as (S)— or (R)—1-ethyl-2-methyl propyl;

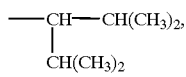

also referred to as 1-isopropyl-2-methyl butyl; or

—$C(CH_3)_2$—$CH(CH_3)_2$, also referred to as 1,1-dimethyl-2-methyl propyl

—$CH(CH_3)_2$, also referred to as isopropyl

—$CH(CH_3)CH_2CH_3$, also referred to as sec-butyl, (S)— or (R)—

—$CH(CH_3)CH(CH_3)_2$, also referred to as 1,2-dimethylpropyl.

In another embodiment, the second compound in the pharmaceutical composition of the invention is a compound of Formula I in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tert-butylglycyl; D is prolyl, thiazolidinyl-4-carbonyl, 3,4-dehydroprolyl; E is prolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$–$C_4$ alkoxy and $R^6$ is a monovalent radical such as a $C_3$–$C_{10}$ cycloalkyl group (e.g. cyclobutyl, cyclopentyl, cyclohexyl, or 1-methylcyclopentyl, or 1-methylcyclohexyl or bicyclo[3.3.0]octa-1-yl); a (1)- or (2)-adamantyl group; $(CH_2)_v$-phenyl with v=1 or α,α-dimethylbenzyl.

Figure 1D:
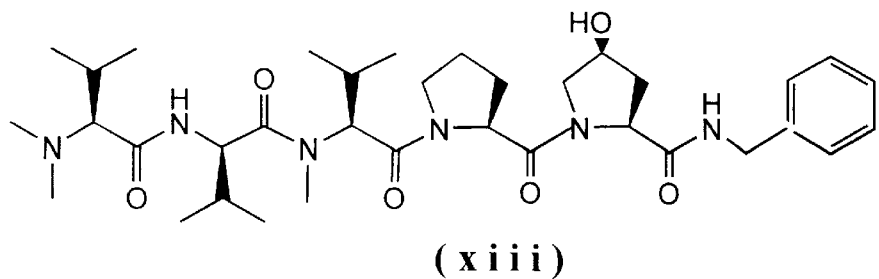
Figure 1D:
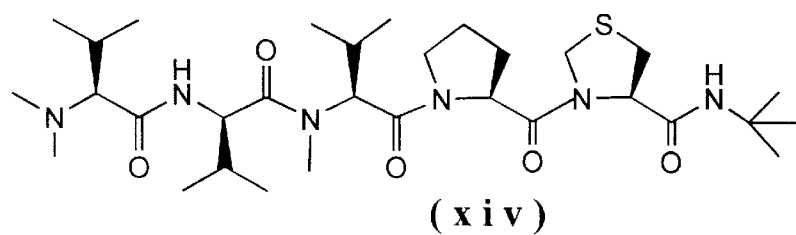
Figure 1D:
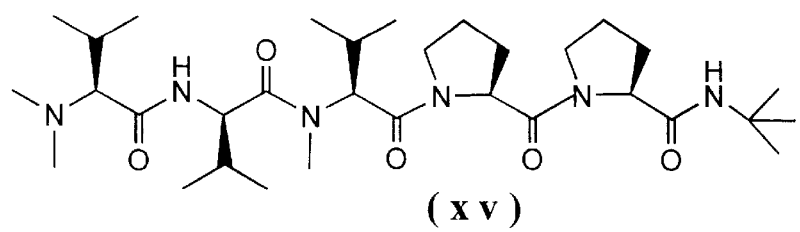
Figure 1D:
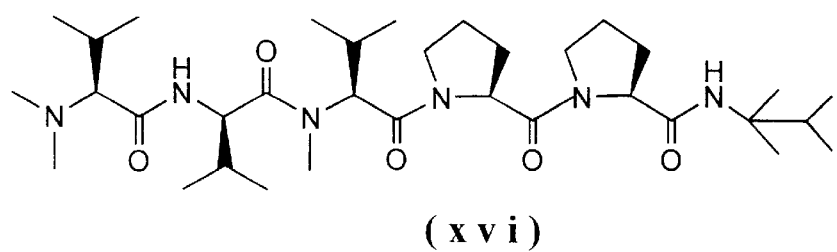
Figure 1D:
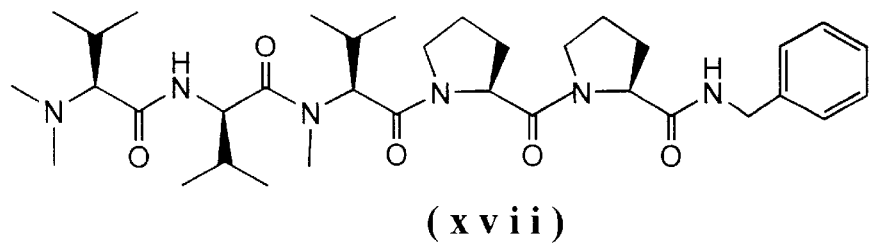
Figure 1A:
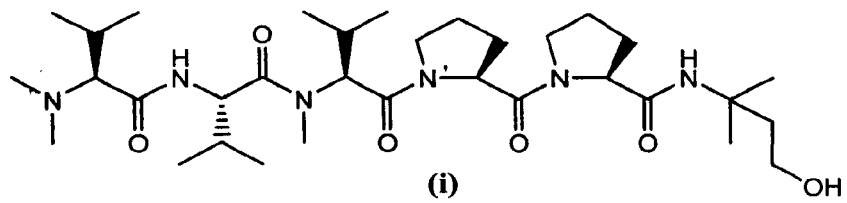
Figure 1A:
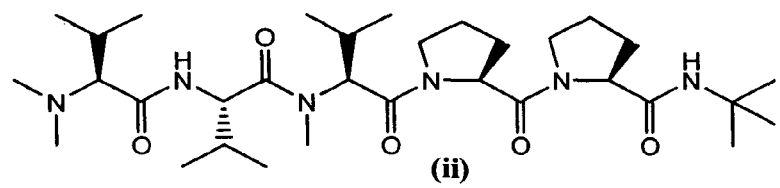
Figure 1A:
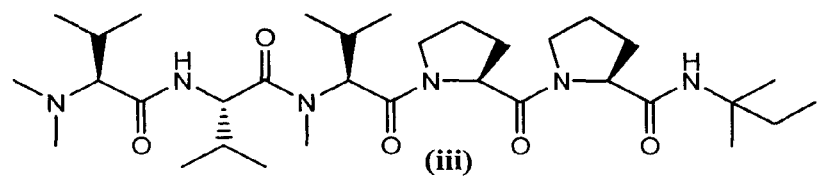
Figure 1A:
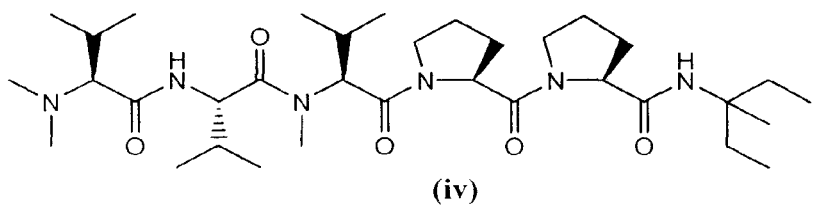

In a further embodiment, the second compound in the pharmaceutical composition of the invention is a compound of Formula I in which $R^1$ and $R^2$ are each methyl; X is isopropyl; s is 1; t and u are each 0; A is valyl; B is N-methylvalyl; D is prolyl; E is prolyl; and K is a substituted amino moiety having the formula $R^5$—N—$R^6$ wherein $R^5$ is benzyl and $R^6$ is hydrogen. This compound corresponds to compound (xvii) depicted in FIG. 1D. The results of the use of compound (xvii) of Formula I, in combination with paclitaxel are presented in Tables 1-4.

The pharmaceutical compositions of the present invention may optionally contain a pharmaceutically acceptable carrier. Pharmaceutically acceptable carriers are well known to those who are skilled in the art. The choice of a carrier will be determined in part by the particular compounds in the combination, as well as by the particular method used to administer the pharmaceutical composition. Accordingly, there is a wide variety of suitable formulations of the pharmaceutical compositions of the present invention. For example, paclitaxel (Taxol®) is available as a sterile non-pyrogenic solution which includes polyoxyethylated castor oil (Cremophor® EL) and dehydrated alcohol, USP.

In another aspect, the present invention comprises a method for partially or totally inhibiting formation of, or otherwise treating (e.g., reversing or inhibiting the further development of) solid tumors (e.g., tumors of the lung, breast, colon, prostate, bladder, rectum, or endometrium) or hematological malignancies (e.g., leukemias, lymphomas) in a mammal, for example, a human, by administering to the mammal an effective amount of a first compound which is paclitaxel, taxotere or a modified taxane or taxoid analog and administering an effective amount of a second compound, which is a compound of Formula I.

The two compounds are administered in combination according to the invention. The term in combination in this context means that the drugs are given either simultaneously or sequentially. If given sequentially, one of the two compounds is usually detectable in the serum of the subject at the onset of administration of the other compound. In one embodiment, a compound of Formula I is administered first, followed by administration of the above described first compound, such as paclitaxel. In a specific embodiment, paclitaxel is administered about one hour after administration of a compound of Formula I.

Alternatively, the first compound and the second compound can be administered simultaneously, or the first compound could be administered first, followed by administration of a second compound, which is a compound of Formula I.

The first and the second compounds may be administered alone or with a pharmaceutically accepted carrier or diluent appropriate for the desired route of administration. Administration can be by any of the means which are conventional for pharmaceutical, preferably oncological, agents, including oral and parenteral means such as subcutaneously, intravenously, intramuscularly, intraperitoneally, nasally or rectally. Such pharmaceutical compositions may also contain other therapeutically active ingredients.

The dosage administered to the mammal, such as a human, includes a combination of an effective amount of a compound of Formula I and an effective amount of paclitaxel, taxotere or modified taxane or taxoid analog, as described herein. For a particular condition or method of treatment, the dosage can be determined empirically, using known methods, and will depend upon factors such as the biological activity, mechanism of action, cross resistance, overlapping toxicity and toxicity profile of the particular compounds employed; the means of administration; the age, health and body weight of the recipient; the nature and extent of the symptoms; the frequency of treatment; the administration of other therapies; and the effect desired.

A typical daily dose of the compounds of Formula I will be from about 5 to about 250 milligrams per kilogram of body weight by oral administration and from about 1 to about 100 milligrams per kilogram of body weight by parenteral administration. A typical daily dose of paclitaxel, taxotere or a modified taxane or taxoid analog will generally be from 5 to about 250 milligrams per kilogram.

The first and the second compounds of the present invention can be administered in conventional solid or liquid pharmaceutical administration forms, for example, uncoated or (film)coated tablets, capsules, powders, granules, suppositories or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/or propellant gases (cf. H. Sücker et al.: Pharmazeutische Technologie, Thieme-Verlag, Stuttgart, 1978). The administration forms obtained in this way typically contain from about 1 to about 90% by weight of the active substance.

The compounds of Formula I are described in detail above. In a particular embodiment, the method of the invention uses a compound of Formula I in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tert-butylglycyl; D is prolyl, thiazolidinyl-4-carbonyl or 3,4-dehydroprolyl; E is prolyl, thiazolidinyl-4-carbonyl, homoprolyl, 3,4-dehydroprolyl or hydroxyprolyl; and K is a substituted or unsubstituted amino moiety having the formula $R^5$—N—$R^6$.

In a further embodiment, the method of the invention uses a compound of Formula I in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tert-butylglycyl; D is prolyl, thiazolidinyl-4-carbonyl or 3,4-dehydroprolyl; E is prolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$–$C_4$ alkoxy and $R^6$ is a $C_1$–$C_{12}$ linear or branched alkyl group or $C_1$–$C_{12}$ linear or branched hydroxyalkyl group represented, for example, by the following monovalent radicals:

—C(CH$_3$)$_2$—CH$_2$—CH$_2$—OH, also referred to as 3-hydroxy-1,1-dimethylpropyl;

—C(CH$_3$)$_3$, also referred to as tert-butyl;

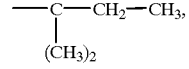

also referred to as 1,1-dimethyl propyl;

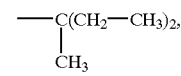

also referred to as 1-methyl-1-ethyl propyl;

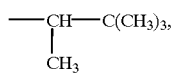

also referred to as (S)— or (R)—1-methyl-2,2-dimethyl propyl;

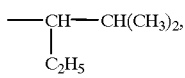

also referred to as (S)— or (R)—1-ethyl-2-methyl propyl;

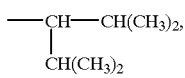

also referred to as 1-isopropyl-2-methyl butyl; or
—C(CH$_3$)$_2$—CH(CH$_3$)$_2$, also referred to as 1,1-dimethyl-2-methyl propyl
—CH(CH$_3$,)$_2$, also referred to as isopropyl
—CH(CH$_3$)CH$_2$CH$_3$, also referred to as sec-butyl, (S)— or (R)—
—CH(CH$_3$)CH(CH$_3$)$_2$, also referred to as 1,2-dimethylpropyl.

In another embodiment, the method of the invention uses a compound of Formula I in which $R^1$ and $R^2$ are each methyl or ethyl; X is isopropyl, sec-butyl or tert-butyl; s is 1; t and u are each 0; A is valyl, isoleucyl or 2-tert-butylglycyl; B is N-methylvalyl, 1-isoleucyl or 2-tert-butylglycyl; D is prolyl, thiazolidinyl-4-carbonyl, 3,4-dehydroprolyl; E is prolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$-$C_4$ alkoxy and $R^6$ is a monovalent radical such as a $C_3$-$C_{10}$ cycloalkyl group (e.g. cyclobutyl, cyclopentyl, cyclohexyl, 1-methylcyclopentyl, 1-methylcyclohexyl or bicyclo [3.3.0]octa-1-yl); a (1)- or (2)-adamantyl group; (CH$_2$)v-phenyl with v=1 or α,α-dimethylbenzyl.

In a further embodiment, the method of the invention uses a compound of Formula I in which $R^1$ and $R^2$ are each methyl; X is isopropyl; s is 1; t and u are each 0; A is valyl; B is N-methylvalyl; D is prolyl; E is prolyl; and K is a substituted amino moiety having the formula $R^5$—N—$R^6$ wherein $R^5$ is benzyl and $R^6$ is hydrogen. This compound corresponds to compound (xvii) depicted in FIG. 1D. The results of the use of compound (xvii) of Formula I, in combination with paclitaxel are presented in Tables 1–4.

Synthetic Methods

The compounds of Formula I can be prepared by known methods of peptide synthesis such as those described herein and, in U.S. patent application Ser. No. 08/470,453 filed Jun. 7, 1995, the teachings of which are incorporated herein by reference. The peptides can be assembled sequentially from individual amino acids or by linking suitable small peptide fragments. In sequential assembly, the peptide chain is extended stepwise, starting at the C-terminus, by one amino acid per step. In fragment coupling, fragments of different lengths can be linked together, and the fragments can also be obtained by sequential assembly from amino acids or by fragment coupling of still shorter peptides.

In both sequential assembly and fragment coupling it is necessary to link the units by forming an amide linkage, which can be accomplished via a variety of enzymatic and chemical methods. The methods described herein for formation of peptidic amide linkages, are also suitable for the formation of non-peptidic amide linkages.

Chemical methods for forming the amide linkage are described in detail in standard references on peptide chemistry, including Müller, Methoden der organischen Chemie Vol. XV/2, 1–364, Thieme Verlag, Stuttgart, (1974); Stewart and Young, Solid Phase Peptide Synthesis, 31–34 and 71–82, Pierce Chemical Company, Rockford, Ill. (1984); Bodanszky et al., Peptide Synthesis, 85–128, John Wiley & Sons, New York, (1976); Practice of Peptide Synthesis, M. Bodansky, A. Bodansky, Springer-Verlag, 1994 and other standard works in peptide chemistry. Preferred methods include the azide method, the symmetric and mixed anhydride method, the use of in situ generated or preformed active esters, the use of urethane protected N-carboxy anhydrides of amino acids and the formation of the amide linkage using coupling reagents, such as dicyclohexylcarbodiimide (DCC), diisopropylcarbodiimide (DIC), 1-ethoxycarbonyl-2-ethoxy-1,2-dihydroquinoline (EEDQ), pivaloyl chloride, 1-ethyl-3-(3-dimethylaminopropyl) carbodiimide hydrochloride (EDCI), n-propane-phosphonic anhydride (PPA), N,N-bis (2-oxo-3-oxazolidinyl)amido phosphoryl chloride (BOP-Cl), bromo-tris-pyrrolidinophosphonium hexafluorophosphate (PyBrop), diphenylphosphoryl azide (DPPA), Castro's reagent (BOP, PyBop), O-benzotriazolyl-N,N,N',N'-tetramethyluronium alts (HBTU), O-azabenzotriazolyl-N,N,N',N'-etramethyluronuim salts (TATU), diethylphosphoryl cyanide (DEPCN), 2,5-diphenyl-2,3-dihydro-3-oxo-4-hydroxythiophene dioxide (Steglich's reagent; HOTDO), and 1,1'-carbonyldiimidazole (CDI). The coupling reagents can be employed alone or in combination with additives such as N,N-dimethyl-4-aminopyridine (DMAP), N-hydroxy-benzotriazole (HOBt), N-hydroxybenzotriazine (HOOBt), N-hydroxysuccinimide (HOSU) or 2-hydroxypyridine.

Although the use of protecting groups is generally not necessary in enzymatic peptide synthesis, reversible protection of reactive groups not involved in formation of the amide linkage is necessary for both reactants in chemical synthesis. Three conventional protective group techniques typically used for chemical peptide synthesis are: the benzyloxycarbonyl (Z), the t-butoxycarbonyl (Boc) and the 9-fluorenylmethoxycarbonyl (Fmoc) techniques. Identified in each case is the protective group on the α-amino group of the chain-extending unit. A detailed review of amino-acid protective groups is given by Müller, Methoden der organischen Chemie Vol. XV/1, pp 20–906, Thieme Verlag, Stuttgart (1974).

The units employed for assembling the peptide chain can be reacted in solution, in suspension or by a method similar to that described by Merrifield in J. Amer. Chem. Soc. 85 (1963) 2149. In one method, peptides are assembled sequentially or by fragment coupling using the Z, Boc or Fmoc protective group technique, with one of the reactants in the Merrifield technique being bonded to an insoluble polymeric support (also called resin hereinafter). This typically entails assembling the peptide sequentially on the polymeric support using the Boc or Fmoc protective group technique, with the growing peptide chain covalently bonded at the C terminus to the insoluble resin particles. This procedure allows the removal of reagents and by-products by filtration, eliminating the need to recrystallize intermediates.

The protected amino acids can be linked to any suitable polymer, which must be insoluble in the solvents used and have a stable physical form which permits filtration. The polymer must contain a functional group to which the first protected amino acid can be covalently attached. A wide variety of polymers are suitable for this purpose, for example, cellulose, polyvinyl alcohol, polymethacrylate, sulfonated polystyrene, chloromethylated styrene/divinylbenzene copolymer (Merrifield resin), 4-methylbenzhydrylamine resin (MBHA-resin), phenylacetamidomethyl resin (Pam-resin), p-benzyloxy -benzyl-alcohol-resin, benzhydryl-amine-resin (BHA-resin), 4-(hydroxymethyl)-benzoyl-oxymethyl-resin, the resin of Breipohl et al. (*Tetrahedron Letters* 28 (1987) 565; supplied by BACHEM), 4-(2,4-dimethoxyphenylaminomethyl) phenoxy resin (supplied by Novabiochem) or o-chlorotrityl-resin (supplied by Biohellas).

Solvents suitable for peptide synthesis include any solvent which is inert under the reaction conditions, for example, water, N,N-dimethylformamide (DMF), dimethyl sulfoxide (DMSO), acetonitrile, dichloromethane (DCM), 1,4-dioxane, tetrahydrofuran (THF), N-methyl-2-pyrrolidone (NMP) and mixtures of these solvents.

Peptide synthesis on the polymeric support can be carried out in a suitable inert organic solvent in which the amino acid derivatives and starting materials employed are soluble. Particularly useful solvents are, for example, DMF, DCM, NMP, acetonitrile, DMSO and mixtures thereof, due to their resin swelling properties.

Following synthesis, the peptide is removed (commonly referred to as cleaved) from the polymeric support. The conditions under which this cleavage is accomplished are well known in the art of peptide synthesis and depend in part on the type of resin employed. The cleavage reactions most commonly used are acid- or palladium-catalyzed, the acid catalyzed cleavage being conducted in, for example, liquid anhydrous hydrogen fluoride, anhydrous trifluoromethane-sulfonic acid, dilute or concentrated trifluoroacetic acid, and acetic acid/dichloromethane/trifluoroethanol mixtures. The palladium-catalyzed cleavage can be carried out in THF or THF-DCM-mixtures in the presence of a weak base such as morpholine. Certain protecting groups are also cleaved off under these conditions.

Partial deprotection of the peptide may also be necessary prior to certain derivatization reactions. For example, peptides dialkylated at the N-terminus can be prepared either by coupling the appropriate N,N-di-alkylamino acid to the peptide in solution or on the polymeric support or by reductive alkylation of the resin-bound peptide in DMF/1% acetic acid with NaCNBH$_3$ and the appropriate aldehyde or by hydrogenation of the peptide in solution in the presence of aldehyde or ketone and Pd/C.

The various non-naturally occurring amino acids as well as the various non-amino acid moieties disclosed herein may be obtained from commercial sources or synthesized from commercially-available materials using methods known in the art. For example, amino acid building blocks with R$^1$ and R$^2$ moieties can be prepared according to E. Wuensch, Huben Weyl, *Methoden der organischen Chemie* Vol. XV/1, p. 306, Thieme Verlag, Stuttgart (1974) and literature cited therein. Peptides with gamma-or delta-lactam bridges can be prepared by incorporating the appropriate lactam-bridged dipeptide units (R. Freidinger, *J. Org. Chem.* (1982) 104–109) into the peptide chain.

Peptides with thiazole-, oxazol-, thiazolin- or oxazolin-containing dipeptide building blocks can be prepared by incorporating the appropriate dipeptidic units (P. Jouin et al., *Tetrahedron Letters* (1992), pp. 2087–2810; P. Wipf et al., *Tetrahedon Letters* (1992), pp. 907–910; W. R. Tully, *J.* *Med. Chem.* (1991), p 2065; *Synthesis* (1987), p 235) into the peptide chain.

The following procedures are intended to illustrate methods useful for preparation of compounds of Forumla I. When applicable, amino acids are abbreviated using the known three letter codes. Other meanings used are: Me$_2$Val=N,N-dimethylvaline, MeVal=N-methylvaline, TFA=trifluoroacetic acid, Ac=acetic acid, Bu=butyl, Et=ethyl, Me=methyl, Bzl=benzyl, Nal=3-naphthylalanine, Cha=3-cyclohexylalanine, Npg=neopentyl glycine, Abu=2-amino butyryl, Dab=2,4-diaminobutyryl, iPr=isopropyl General Synthetic Procedures I. Compounds of Formula I of the present invention are either synthesized by classical solution synthesis using standard Z- and Boc-methodology as described above or by standard methods of solid-phase synthesis on a completely automatic model 431A synthesizer supplied by APPLIED BIOSYSTEMS. The apparatus uses different synthetic cycles for the Boc and Fmoc protective group techniques.

In the case of solid phase synthesis, the N,N-dialkyl-penta- or hexapeptide acids are liberated from the solid support and further coupled with the corresponding C-terminal amines in solution. BOP-Cl and PyBrop were used as reagents for coupling of the amino acid following the N-methylamino acids. The reaction times were correspondingly increased. For reductive alkylation of the N-terminus, the peptide-resin was deprotected at the N terminus and then reacted with a 3-fold molar excess of aldehyde or ketone in DMF/1% acetic acid with addition of 3 equivalents of NaCNBH$_3$. After the reaction was complete (negative Kaiser test) the resin was washed several times with water, isopropanol, DMF and dichloromethane.

In solution synthesis, the use of either Boc-protected amino acid NCAs (N-tert-butyloxycarbonyl-amino acid-N-carboxy-anhydrides), Z-protected amino acid NCAs (N-benzyloxycarbonyl-amino acid-N-carboxy-anhydrides), or the use of pivaloylchloride as condensing agent respectively is most advantageous for coupling of the amino acid following the N-methylamino acids. Reductive alkylation of the N terminus can, for example, be achieved by reaction of the N-terminally deprotected peptides or amino acids with the corresponding aldehydes or ketones using NaCNBH$_3$ or hydrogen, Pd/C.

a) Synthetic cycle for the Boc protective group technique:
1. 30% trifluoroacetic acid in DCM 1×3 min
2. 50% trifluoroacetic acid in DCM 1×1 min
3. DCM washing
4. 5% diisopropylethylamine in DCM 5×1 min
5. 5% diisopropylethylamine in NMP 1×1 min
6. NMP washing 5×1 min
7. Addition of preactivated protected amino acid (DCC and 1 equivalent of HOBt in NMP/DCM);
   Peptide coupling (1st part) 1×30 min
8. Addition of DMSO to the reaction mixture until it contains 206 DMSO by volume;
   Peptide coupling (2nd part) 1×16 min
9. Addition of 3.8 equivalents of diisopropylethylamine to the reaction mixture;
   Peptide coupling (3rd part) 1×7 min
10. DCM washing 3×1 min
11. If conversion is incomplete, repetition of coupling (back to 6)

12. 10% acetic anydride, 5% diisopropylethylamine in DCM 1×2 min
13. 10% acetic anhydride in DCM 1×4 min
14. DCM washing 4×1 min
15. Back to 1.

BOP-Cl and PyBrop were used as reagents for coupling of the amino acid following N-methylamino acids. The reaction times were correspondingly increased. In solution synthesis, the use of either Boc-protected amino acid NCAs (N-tert-butyloxycarbonyl-amino acid-N-carboxy-anhydrides) or Z-protected amino acids NCAs respectively is most advantageous for this type of coupling.

b) Synthetic cycle for the Fmoc protective group technique:
1. DMF washing 1×1 min
2. 20i piperidine in DMF 1×4 min
3. 20% piperidine in DMF 1×16 min
4. DMF washing 5×1 min
5. Addition of the preactivated protected amino acid (activation by 1 equivalent of TBTU and 5 equivalents of DIPEA in DMF);
   Peptide coupling 1×61 min
6. DMF washing 3×1 min
7. If conversion is incomplete, repetition of coupling (back to 5)
8. 10% acetic anhydride in DMF 1×8 min
9. DMF washing 3×1 min
10. Back to 2.

BOP-Ci and PyBrop were used as reagents for coupling on the amino acid following the N-methylamino acids. The reaction times were correspondingly increased.

II. Reductive Alkylation of the N-terminus

The peptide-resin prepared in Ia or Ib above was deprotected at the N-terminus (steps 2–4 in Ib or 1–6 in 1a) and then reacted with a 3-fold molar excess of aldehyde or ketone in DMF/1% acetic acid with addition of 3 equivalents of $NaCNBH_3$. After reaction was complete (negative Kaiser test) the resin was washed several times with water, isopropanol, DMF and dichloromethane.

III. Workup of the peptide-resins obtained as in Ia and II

The peptide-resin was dried under reduced pressure and transferred into a reaction vessel of a TEFLON HF apparatus (supplied by PENINSULA). Addition of a scavenger, for example, anisole (1 ml/g of resin), and in the case of tryptophan-containing peptides of a thiol to remove the indolic formyl group, for example, ethanedithiol (0.5 ml/g of resin), was followed by condensing in hydrogen fluoride (10 ml/g of resin) while cooling with liquid $N_2$. The mixture was allowed to warm to 0° C. and stirred at this temperature for 45 minutes. The hydrogen fluoride was then stripped off under reduced pressure, and the residue was washed with ethyl acetate in order to remove remaining scavenger. The peptide was extracted with 30% acetic acid and filtered, and the filtrate was lyophilized.

IV. Work-up of the peptide-resins obtained as in Ib and II

The peptide-resin was dried under reduced pressure and then subjected to one of the following cleavage procedures, depending on the amino acid composition (Wade, Tregear, Howard Florey Fmoc Workshop Manual, Melbourne 1985).

| TFA | Scavenger | Reaction time |
|---|---|---|
| 1. 95% | 5% water | 1.5 h |
| 2. 95% | 5% ethanethiol/anisole (1:3) | 1.5 h |

The suspension of the peptide-resin in the suitable TFA mixture was stirred at room temperature for the stated time and then the resin was filtered off and washed with TFA and DCM. The filtrate and the washings were concentrated, and the peptide was precipitated by addition of the diethyl ether. After cooling in an ice bath, the precipitate was filtered off, taken up in 30% acetic acid and lyophilized.

V. When an o-chlorotrityl-resin (supplied by Biohellas) is used, the suspension of the peptide-resin in an acetic acid/trifluoroethanol/dichloromethane mixture (1:1:3) is stirred at room temperature for 1 h. The resin is then filtered off with suction and thoroughly washed with the cleavage solution. The combined filtrates are concentrated in vacuo and treated with water. The precipitated solid is removed by filtration or centrifugation, washed with diethyl ether and dried under reduced pressure.

VI. Purification and characterization of the peptides

Purification was carried out by gel chromatography (SEPHADEX G-10, G-15/10% HOAc, SEPHADEX LH20/MeOH) medium pressure chromatography (stationary phase: HD-SIL C-18, 20–45 micron, 100 Angstrom; mobile phase: gradient with A=0.1% TFA/MeOH, B=0.1% TFA/water) or preparative HPLC (stationary phase: water Delta-Pak C-18, 15 micron, 100 Angstrom; mobile phase: gradient with A=0.1% TFA/MeOH, B=0.1% TFA/water).

The purity of the resulting products was determined by analytical HPLC (stationary phase: 100 2.1 mm VYDAC C-18, 51, 300 Angstrom; mobile phase: acetonitrile-water gradient, buffered with 0.1% TFA, 40° C.).

Characterization was by amino acid analysis and fast atom bombardment mass spectroscopy.

Specific Synthetic Procedures

EXAMPLE 1A

N,N-dimethyl-Val-Val-N-methyl-Val-Pro-Pro-Val-Phe-$NH_2$ 1.98 g of Fmoc-RINK-resin (substitution 0.46 mmol/g), corresponding to a batch size of 0.84 mmol, were reacted as in Ib above with 1.26 mmol each of Fmoc-Phe-OH Fmoc-Val-OH Fmoc-Pro-OH Fmoc-Pro-OH Fmoc-N-methyl-Val-OH Fmoc-Val-OH Fmoc-Val-OH The amino acid following the N-methyl amino acid was coupled on with PyBrop as coupling reagent. After the iterative synthetic cycles were completed, the peptide-resin underwent N-terminal deprotection (steps 2-4 in Ib), and was further reacted with aqueous formaldehyde solution as in II and then dried under reduced pressure. The resulting resin was subjected to TFA cleavage as in IV. The crude product (590 mg) was purified by gel filtration (SEPHADEX-LH-20). The yield was 295 mg.

EXAMPLE 1A

Example 1 can also be prepared via classical solution phase methodology. The synthesis of N,N-dimethyl-Val-Val-N-methyl-Val-Pro-Pro-Val-Phe-$NH_2$ and its associated intermediates is described in the following paragraph.

a) Z-MeVal-Pro-OMe 66.25 g (250 mmol) of Z-MeVal—OH were dissolved in 250 ml of dry dichloromethane. After addition of 36.41 ml (262.5 mmol) of triethylamine, the reaction mixture was cooled to −250° C. and 32.37 ml (262.5 mmol) pivaloyl chloride were added. After stirring for 2.5 hours, 41.89g (250 mmol) of H-Pro-OMe-HCl in 250 ml of dichloromethane, neutralized with 36.41 ml (262.5 mmol) triethylamine at 0° C., were added to the reaction mixture. Stirring was continued for 2 h at −250° C. and overnight at room temperature. The reaction mixture was diluted with dichloromethane and thoroughly washed with saturated aqueous NaHCO$_3$ solution (3×), water (1×), 5% citric acid (3×) and saturated NaCl solution. The organic phase was dried over sodium sulfate, filtered and evaporated to dryness. The residue (91.24 g) was stirred with petroleum ether overnight and filtered. 62.3 g of product were obtained.

b) H-MeVal-Pro-OMe 48.9 g (130 mmol) Z-MeVal-Pro-OMe were dissolved in 490 ml of methanol. After addition of 10.9 ml (130 mmol) concentrated hydrochloric acid and 2.43 g of 10% palladium/charcoal, the reaction mixture was hydrogenated. Filtration and evaporation to dryness yielded 36.43 g of product.

c) Z-Val-MeVal-Pro-OMe 18.1 g (65 mmol) of H-MeVal-Pro-OMe, 21.6 g (78 mmol) Z-Val-N-carboxyanhydride and 22.8 ml (130 mmol) diisopropylethylamine were stirred in 110 ml of DMF at 40° C. for 2 days. After evaporation of DMF, dichloromethane was added and the organic phase washed with saturated aqueous NaHCO$_3$ solution (3×), water (1×) 5% citric acid (3×) and saturated NaCl solution. The organic phase was dried over sodium sulfate, filtered and evaporated to dryness. The product (29.3 g) was obtained as a viscous oil.

d) H-Val-MeVal-Pro-OMe 29.3 g (61.6 mmol) of Z-Val-MeVal-Pro-OMe were dissolved in 230 ml of methanol. After addition of 1.15 g of 10% palladium/charcoal, the reaction mixture was hydrogenated. Filtration and evaporation to dryness yielded 21.96 g of product.

e) Z-Val-Val-MeVal-Pro-OMe 15.29 g (61 mmol) of Z-Val-OH and 21.96 g (61 mmol) of H-Val-MeVal-Pro-OMe were dissolved in 610 ml of dichloromethane and cooled to 0° C. After addition of 8.16 mol(73.2 mmol) of N-methylmorpholine, 2.77 g (20.3 mmol) of HOBt and 11.74g (61 mmol) of EDCI, the reaction mixture was stirred overnight at room temperature, diluted with dichloromethane and thoroughly washed with saturated aqueous NaHCO$_3$ solution (3×), water (1×), 5% citric acid (3×) and saturated NaCl solution. The organic phase was dried over sodium sulfate, filtered and evaporated to dryness to yield 31.96 g of the product.

f) Z-Val-Val-MeVal-Pro-OH 31.96 g (57 mmol) of Z-Val-Val-MeVal-Pro-OMe were dissolved in 250 ml of methanol. 102.6 ml of a 1N LiOH solution was added and the mixture stirred overnight at room temperature. After addition of 500 ml of water, the aqueous phase was washed three times with ethyl acetate. The organic phase was dried over sodium sulfate, filtered and evaporated to dryness yielding 30.62 g of the desired product as a white solid.

g) Z-Val-Val-MeVal-Pro-Pro-Val-Phe-NH$_2$ 25 g (43.3 mmol) of Z-Val-Val-MeVal-Pro-OH and 15.59 g (43.3 mmol) of H-Pro-Val-Phe-NH$_2$ were suspended in 430 ml of dry dichloromethane. After cooling to 0° C., 5.81 ml (52 mmol) N-methylmorpholine, 1.97 g (15 mmol) of HOBt and 8.33 g (43.3 mmol) of EDCI were added and the reaction mixture stirred overnight at room temperature. The solvents were evaporated, the residue dissolved in 640 ml of dichloromethane and thoroughly washed with saturated aqueous NaHCO$_3$ solution (4×), water (1×), 5% citric acid (3×) and saturated NaCl solution. The organic phase was dried over sodium sulfate, filtered and evaporated to dryness to yield 33.04 g of the product. The crude product was chromatographed on a silica gel column with 20% MeOH/hexane. 18.32 g of the desired product were obtained.

h) N,N-dimethyl-Val-Val-MeVal-Pro-Pro-Val-Phe-NH$_2$ 18.32 g of Z-Val-Val-MeVal-Pro-Pro-Val-Phe-NH$_2$ were dissolved in 80 ml of methanol. 0.4 g of 10% palladium/carbon were added under nitrogen atmosphere and the reaction mixture hydrogenated at room temperature for 4 hours. After addition of 6.22 ml (81.24 mmol) of a 37% aqueous formaldehyde solution, hydrogenation was continued for 5 hours. Filtration and evaporation of the solvent gave rise to 15.6 g of crude product. Further purification was achieved by dissolving the peptide in water, adjusting the pH to 2 and extracting the aqueous phase three times with ethyl acetate. The aqueous phase was then adjusted to pH 8–9 and extracted four times with ethyl acetate. The organic phase was washed with water and dried over sodium sulfate, filtered and evaporated to yield 11.3 g of purified product as a white powder. The compound was characterized by fast atom bombardment mass spectrometry ([M+H]$^+$=797).

EXAMPLE 2A

N,N-dimethyl-Val-Val-NMe-Val-Pro-{1-[thiazol-(2)-yl]-2-phenyl}-ethylamide 4.11 g of Fmoc-Pro-p-alkoxybenzyl-alcohol-resin (substitution 0.73 mmol/g), corresponding to a batch size of 3 mmol, were reacted as in Ib with 4.5 mmol each of Fmoc-N-MeVal-OH Fmoc-Val-OH Fmoc-Val-OH The amino acid following the N-methylamino acid was in this case reacted with double coupling using PyBrop or Bop-Cl with increased reaction times. After the synthesis was complete, the peptide-resin underwent N-terminal deprotection (Steps 2–4 in Ib), and was further reacted with aqueous formaldehyde solution as in II and then dried under reduced pressure. The resin obtained in this way was subjected to TFA cleavage as in IV. The crude product (750 mg) was employed directly for the next coupling. 100 mg of this compound were reacted with 45 mg of (S)-2-[1-amino-2-phenylethyl]thiazole and 230 mg of PyBop with the addition of 192 microliters of DIPEA in DMF at room temperature for 2 days. The reaction mixture was purified by gel chromatography (SEPHADEX LH-20, methanol) and the product fractions were combined. 83 mg of product were obtained.

EXAMPLE 1B

Me$_2$Val-Val-MeVal-Pro-Pro-NHCH(CH$_3$) 2 a) Z-MeVal-Pro-OMe 66.25 g (250 mmol) Z-MeVal-OH were dissolved in 250 ml dry dichloromethane. After addition of 36.41 ml (262.5 mmol) triethylamine, the reaction mixture was cooled to −25° C. and 32.27 ml (262.5 mmol) pivaloyl chloride were added. After stirring for 2.5 h, 41.89 g (250 mmol) H-Pro-OMe×HCl in 250 ml dichloromethane, neutralized with 36.41 ml (262.5 mmol) triethylamine at 0° C., were added to the reaction mixture. Stirring continued for 2 h at −25° C. and overnight at room temperature. The reaction mixture was diluted with dichloromethane and thoroughly washed with saturated aqueous NaHCO$_3$ solution (3×), water (1×), 5S citric acid (3×) and saturated NaCl solution. The organic phase was dried over sodium sulfate, filtered and evaporated to dryness. The residue (91.24 g) was stirred with petroleum ether overnight and filtered. 62.3 g of product were obtained.

b) H-MeVal-Pro-OMe 48.9 g (130 mmol) Z-MeVal-Pro-OMe were dissolved in 490 ml methanol. After addition of 10.9 ml (130 mmol) concentrated hydrochloric acid and 2.43 g 10% Palladium/charcoal, the reaction mixture was hydrogenated. Filtration and evaporation to dryness yielded 36.43 g of the product.

c) Z-Val-MeVal-Pro-OMe 18.1 g (65 mmol) H-MeVal-Pro-OMe, 21.6 g (78 mmol) Z-Val-N-carboxyanhydride and 22.8 ml (130 mmol) diisopropylethylamine were stirred in 110 ml DMF at 40° C. for 2 d. After evaporation of DMF, dichloromethane was added and the organic phase washed with saturated aqueous NaHCO$_3$ solution (3×), water (1×), 5 citric acid (3×) and saturated NaCl solution. The organic phase was dried over sodium sulfate and evaporated to dryness. The product (29.3 g) was obtained as a viscous oil.

d) H-Val-MeVal-Pro-OMe 29.3 g (61.6 mmol) of Z-Val-MeVal-Pro-OMe were dissolved in 230 ml methanol. After addition of 1.15 g 10% Palladium/charcoal, the reaction mixture was hydrogenated. Filtration and evaporation to dryness yielded 21.96 g of the product.

e) Z-Val-Val-MeVal-Pro-OMe 15.29 g (61 mmol) Z-Val-OH and 21.96 g (61 mmol) H-Val-MeVal-Pro-OMe were dissolved in 610 ml dichloromethane and cooled to 0° C. After addition of 8.16 ml (73.2 mmol) N-Methylmoropholine, 2.77 g (20.3 mmol) HOBt and 11.74 g (61 mmol) EDCI, the reaction mixture was stirred overnight at room temperature, diluted with dichloromethane and thoroughly washed with saturated aqueous NaHCO$_3$ solution (3×), water (1×), 5% citric acid (3×) and saturated NaCl solution. The organic phase was dried over sodium sulfate, filtered and evaporated to dryness to yield 31.96 g of the product.

f) Z-Val-Val-MeVal-Pro-OH 31.96 g (57 mmol) Z-Val-Val-MeVal-Pro-OMe were dissolved in 250 ml methanol. 102.6 ml of a 1 N LiOH solution was added and the mixture stirred overnight at room temperature. After addition of 500 ml water, the aqueous phase was washed three times with ethyl acetate, adjusted to pH 2 at 0° C. and extracted three times with ethyl acetate. The organic phase was dried over sodium sulfate, filtered and evaporated to dryness yielding 30.62 g of the desired product as a white solid.

g) Z-Val-Val-MeVal-Pro-Pro-NHCH(CH$_3$)$_2$ 2 g (3.35 mmol) Z-Val-Val-MeVal-Pro-OH and 0.664 g (3.35 mmol) H-Pro-NHCH(CH$_3$)$_2$ were dissolved in 34 ml of dry dichloromethane. After cooling to 0° C., 1.35 ml (12.1 mmol) N-methylmorpholine, 0.114 g (0.84 mmol) HOBt and 0.645 g (3.35 mmol) EDCI were added and the reaction mixture stirred overnight at room temperature. 80 ml dichloromethane were added and the organic phase thoroughly washed with saturated aqueous NaHCO$_3$ solution (3×), water (1×), 5% citric acid (3×) and saturated NaCl solution (1×). The organic phase was dried over sodium sulfate, filtered and evaporated to dryness to yield 1.96 g of the product which was used in the next reaction without further purification.

h) Me$_2$Val-Val-MeVal-Pro-Pro-NHCH(CH$_3$)$_2$ 1.96 g Z-Val-Val-MeVal-Pro-Pro-NHCH(CH$_3$)$_2$ were dissolved in 11 ml methanol. 0.054 g 10% Pd/C were added under nitrogen atmosphere and the reaction mixture hydrogenated at room temperature for 4 h. After addition of 0.86 ml (11.24 mmol) of a 37% aqueous formaldehyde solution and 0.281 g 10% Pd/C, hydrogenation was continued for 5 h. Filtration and evaporation of the solvent gave rise to 2.77 g of crude product. Further purification was achieved by dissolving the peptide in water, adjusting the pH to 2 and extracting the aqueous phase three times with ethyl acetate. The aqueous phase was then adjusted to pH 8–9 and extracted four times with dichloromethane. The organic phase was dried over sodium sulfate, filtered and evaporated to yield 1.37 g of purified product as a white foam. The compound was further purified using medium pressure liquid chromatography (10–50% A in 10 min.; 50–90% A in 320 min.). Fractions containing the product were combined, lyophilized, redissolved in water and the pH adjusted to 9 with 1 N LiOH. After extraction with dichloromethane, the organic phase was dried over sodium sulfate, filtered and evaporated to dryness. Lyophilization led to 500 mg of pure product, which was characterized by fast atom bombardment mass spectrometry ([M+H]$^+$=593).

EXAMPLE 2B

Me$_2$Val-Val-MeVal-Pro-Pro-NHC (CH$_3$)$_3$ a) Z-Val-Val-MeVal-Pro-Pro-NHC(CH$_3$)$_3$ 2 g (3.35 mmol) Z-Val-Val-MeVal-Pro-OH and 0.692 g (3.35 mmol) H-Pro-NHC(CH$_3$)$_3$ were dissolved in 34 ml of dry dichloromethane. After cooling to 0° C., 1.35 ml (12.1 mmol) N-methylmorpholine, 0.114 g (0.84 mmol) HOBt and 0.645 g (3.35 mmol) EDCI were added and the reaction mixture stirred overnight at room temperature. 80 ml dichloromethane were added and the organic phase thoroughly washed with saturated aqueous NaHCO$_3$ solution (3×), water (1×), 5% citric acid (3×) and saturated NaCl solution (1×). The organic phase was dried over sodium sulfate, filtered and evaporated to dryness to yield 1.8 g of the product which was used in the next reaction without further purification.

b) Me$_2$Val-Val-MeVal-Pro-Pro-NHC(CH$_3$)$_3$ 1.8 g Z-Val-Val-MeVal-Pro-Pro-NHC(CH$_3$)$_3$ were dissolved in 10 ml methanol. 0.045 g 10% Pd/C were added under nitrogen atmosphere and the reaction mixture hydrogenated at room temperature for 4 h. After addition of 0.86 ml (11.24 mmol) of a 37% aqueous formaldehyde solution and 0.252 g 10% Pd/C, hydrogenation was continued for 5 h. Filtration and evaporation of the solvent gave rise to 1.82 g of crude product. The compound was further purified using medium pressure liquid chromatography (10–50% A in 10 min.; 50–90% A in 320 min.). Fractions containing the product were combined, lyophilized, redissolved in water and the pH adjusted to 9 with 1 N LiOH. After extraction with dichloromethane, the organic phase was dried over sodium sulfate and evaporated to dryness. Lyophilization led to 547 mg of pure product, which was characterized by fast atom bombardment mass spectrometry ([M+H]$^+$=607).

Evaluation Of Biological Activity

In vivo Methodology

The combination of a compound of Formula I and paclitaxel, taxotere or a modified taxane or taxoid analog was further tested in various preclinical assays for in vivo activity, which are indicative of clinical utility.

The P388 (ascites model), LX-1, CX-1 and PC-3 (human tumor xenograft models for lung, colon and prostate) tumor models are all suitable for use in this invention.

In general, any dosing regimen which appears to provide an acceptable level of antitumor activity for both agents is suitable. Any acceptable method of drug administration can be used in the combination therapy of this invention and can be determined using techniques well known to those of skill in the art. In addition, the drugs can be administered either simultaneously or sequentially, in any order.

P388 Model

The P388 tumor model employs a murine lymphocytic leukemia cell line (See Schabel et al., *Pharmac. Ther. A,*

1:411–435). The P388 tumor cells used in this invention, were harvested from donor mice by peritoneal lavage at day 7 post transplant. 1×10$^6$ P388 tumor cells were then implanted intraperitoneally in a volume of 0.5 ml in mice.

A typical dosing regimen includes initiation of treatment approximately one day post transplant followed by treatment on days 5 and 9 post transplant. Generally the compounds of Formula I are administered intravenously (i.v.) and the paclitaxel, taxotere or modified taxane or taxoid analog is administered intraperitoneally (i.p.).

Therapeutic results of the combinations of the invention against P388 cells, are presented in terms of increase in lifespan reflected by the relative median survival time (MST) of treated (T) versus control (C) group (survival period for untreated mice is generally in the range of 11 to 13 days) and is represented as % T/C values. According to the National Cancer Institute guidelines a % T/C in the range or 128–190% indicates a drug with moderate to good activity. In addition, the Net log Cell Kill is used to compare efficacy of different schedules and combinations, and is calculated as follows:

$$\text{Net log Cell Kill} = \frac{[(T - C) - \text{duration of treatment}] \times 0.332}{\text{Doubling Time}}$$

Where,
Doubling Time=time required for control tumors to double once (0.4 days).
T and C=the median survival time (days) for the control (C) and treated (T) mice.
Duration of treatment with drug
0.332=Derived constant A positive Net log Cell Kill number indicates that fewer tumor cells are present at the end of treatment. A negative number indicates that the tumor was still growing during treatment.

EXAMPLE 3

Combination Treatment Using Compound (xvii) and Paclitaxel in the P388 Tumor Model 1×10$^6$ P388 tumor cells were transplanted intraperitoneally in a volume of 0.5 ml in mice. Treatment was initiated approximately 1 day later followed by treatment on both day 5 and day 9, post transplant. Compound (xvii) was administered IV while paclitaxel was administered IP. Compound (xvii) was administered at either 20, 40 or 60 mg/kg and paclitaxel at either 10, 20 or 30 mg/kg. The dosing was sequential with compouond (xvii) being administered first followed by paclitaxel one hour later.

Results:

The results from Example 3 are shown in Table 1. The data in Table 1 shows that single drug treatment resulted in an optimal % T/C of 175% for compound (xvii) corresponding to a Net log Cell Killing (NlCK) of 0.66 when administered intravenously at a dose of 60 mg/kg and an optimal % T/C of 183% corresponding to a NlCK of 1.33 for paclitaxel when administered intraperitoneally at a dose of 10 mg/kg. For combination drug treatment the data of Table 1 show that the combination of 60 mg/kg (xvii) and 20 mg/kg of paclitaxel resulted in a significant increase in life span (P Value less than 0.001, as determined by the Mann-Whitney Test) and an optimal % T/C value of 242% corresponding to a NlCK of 5.98 with 38% of the animals surviving more than 60 days.

Human Tumor Xenografts Model

Human tumors from lung (LX-1), colon (CX-1) and prostate (PC-3) which had been grown in athymic nude mice were transplanted (xenografted) into new recipient mice, as is well known in the art. The transplanted tumor fragments were approximately 50 mg in size. The day of transplantation was designated as day 0. The combination therapy of the present invention was evaluated for anti-tumor efficacy following administration to the xenograft-bearing mice.

Combination therapy was accomplished by intravenous administration of both drugs. The Q2d×3; 5, 12 and 19 injection schedule was followed with paclitaxel being administered one hour after Compound (xvii). In other words, treatment consisted of 3 cycles, starting on days 5, 12 and 19 post tumor implantation. One cycle of treatment consisted of treatment every other day for a total of three times. The optimal dose for single dose administration of both Compound (xvii) and paclitaxel used in the LX-1 and CX-1 types of human xenograft models tested, can be found in Tables 2–3, with no optimal dose determined with the PC-3 model.

Tumor diameters and body weights were measured twice weekly. Tumor volumes were calculated using the diameters measured with Vernier calipers, and the formula:

(length×width$^2$)/2=mg of tumor weight

Mean tumor weights (MTW) were calculated for each treatment group, and T/C values determined for each group relative to the untreated control tumors.

Results are also presented as Net log Cell Kill and are calculated as follows:

$$\text{Net log Cell Kill} = \frac{[(T - C) - \text{duration of treatment}] \times 0.332}{\text{Doubling Time}}$$

T and C=The median days required for the control and treated tumors to reach a specified tumor size, in this -instance 2000 mm$^3$.
Doubling Time=Time required for control tumors to double in size.
0.332=Derived constant

EXAMPLE 4

Combination Treatment Using Compound 103793 and Paclitaxel in the LX-1 Human Tumor Xenograft Model The Q2d×3; 5, 12 and 19 dosing regimen described above was used in this example. Paclitaxel was administered IV one hour after Compound (xvii) was administered IV. The optimal single dose of both paclitaxel and Compound (xvii) can be determined from Table 2.

TABLE 1

DOSE RESPONSE OF COMPOUND (xvii) WITH AND WITHOUT PACLITAXEL AGAINST THE P388 IN VIVO TUMOR MODEL

| DRUGS Dose (mg/kg) | | | | | | |
|---|---|---|---|---|---|---|
| (xvii) IV | Paclitaxel IP | % Toxic Death | % T/C | Net Log Cell Kill | % 60 Day Cures | Total # Animals |
| 0 | 30 | 8 | 204 | 2.99 | 3 | 36 |
| 0 | 20 | 0 | 175 | 0.66 | 4 | 24 |
| 0 | 10 | 0 | 183 | 1.33. | | 24 |
| 60 | 0 | 0 | 175 | 0.66 | | 42 |

TABLE 1-continued

DOSE RESPONSE OF COMPOUND (xvii) WITH AND WITHOUT
PACLITAXEL AGAINST THE P388 IN VIVO TUMOR MODEL DRUGS
Dose (mg/kg)

| (xvii) IV | Paclitaxel IP | % Toxic Death | % T/C | Net Log Cell Kill | % 60 Day Cures | Total # Animals |
|---|---|---|---|---|---|---|
| 40 | 0 | 0 | 158 | −0.66 | 2 | 42 |
| 20 | 0 | 0 | 158 | −0.66 |   | 42 |
| 60 | 30 | 25 | 217 | 3.98 | 25 | 24 |
| 60 | 20 | 4 | 242 | 5.98 | 38 | 24 |
| 60 | 10 | 0 | 204 | 2.99 |   | 24 |
| 40 | 30 | 21 | 212 | 3.65 | 8 | 24 |
| 40 | 20 | 0 | 212 | 3.65 | 12 | 24 |
| 40 | 10 | 0 | 183 | 1.33 |   | 24 |
| 20 | 30 | 8 | 217 | 3.98 | 25 | 24 |
| 20 | 20 | 0 | 217 | 3.98 | 14 | 22 |
| 20 | 10 | 0 | 183 | 1.33 | 4 | 24 |

Q4Dx3;1 Paclitaxel injected one hour after (xvii)

EXAMPLE 5

Combination Treatment Using Compound 103793 and Paclitaxel in the CX-1 Human Tumor Xenograft Model The Q2dx3; 5, 12 and 19 dosing regimen described above was used in this example. Paclitaxel was administered IV one hour after Compound (xvii) was administered IV. The optimal single dose of both paclitaxel and Compound (xvii) can be determined from Table 3.

EXAMPLE 6

Combination Treatment Using Compound 103793 and Paclitaxel in the PC-3 Human Tumor Xenograft Model The Q2dx3; 5, 12 and 19 dosing regimen described above was used in this example. Paclitaxel was administered IP one hour after Compound (xvii) was administered IV. The optimal single dose of both paclitaxel and Compound (xvii) was not determined.

Results:

The results obtained using the Human Xenograft Model to assess anti-tumor efficacy of the combination therapy of the present invention are presented in Tables 2–4. The data presented represents results from preliminary experiments. The data in Table 2 show that the optimal combination of compound (xvii) and paclitaxel was 15 mg/kg and 10 mg/kg respectively, in the LX-1 model. The combination resulted in some regressions and tumor growth delay. However, the same combination schedule in the CX-1 model did not result in any advantage over the single drug treatment as shown in Table 3.

In the PC-3 model, there was no beneficial effect of the combination as compared to single drug treatment. However, the optimal dose for single dose administration was not determined.

TABLE 2

DOSE RESPONSE OF COMPOUND (xvii) WITH AND WITHOUT
PACLITAXEL AGAINST THE LX-1 IN VIVO TUMOR MODEL.
LX-1#16

DRUGS

| Compound (xvii) (IV) Dose (mg/kg) | Paclitaxel (IV) Dose (mg/kg) | % Toxic Death | MTW d27 % T/C | Net Log Cell Kill | Total # Animals | REGRESSIONS PARTIAL | REGRESSIONS COMPLETE | REGRESSIONS CURE |
|---|---|---|---|---|---|---|---|---|
| 0 | 10 | 0 | 10.5 | −0.374 | 6 | 2 |  |  |
| 25 | 0 | 0 | 3.94 | −0.042 | 6 |  |  |  |
| 15 | 0 | 0 | 12.24 | −0.465 | 6 |  |  |  |
| 7.5 | 0 | 0 | 19.06 | −0.581 | 6 |  |  |  |
| 25 | 10 | 0 | 1.28 | 0.382 | 6 | 4 |  |  |
| 15 | 10 | 17 | 1.92 | 0.589 | 6 | 1 |  |  |
| 7.5 | 10 |  | 4.57 | −0.033 | 6 |  |  |  |

*Q2Dx3;5,12,19 Paclitaxel injected one hour after Compound (xvii).

TABLE 3

DOSE RESPONSE OF COMPOUND (xvii) WITH AND WITHOUT
PACLITAXEL AGAINST THE CX-1 IN VIVO TUMOR MODEL.
CX-1#16

DRUGS

| Compound (xvii) (IV) Dose (mg/kg) | Paclitaxel (IV) Dose (mg/kg) | % Toxic Death | MTW d55 % T/C | Net Log Cell Kill | Total # Animals | REGRESSIONS PARTIAL | REGRESSIONS COMPLETE | REGRESSIONS CURE |
|---|---|---|---|---|---|---|---|---|
| 0 | 10 |  | 38.12 | −0.124 | 6 | 2 |  |  |
| 25 | 0 | 83 |  |  | 6 |  |  |  |
| 15 | 0 |  | 52.87 | −0.313 | 6 |  |  |  |
| 7.5 | 0 |  | 109.7 | −0.763 | 6 |  |  |  |
| 25 | 10 |  | 47.64 | −0.354 | 6 | 2 |  |  |
| 15 | 10 |  | 51.61 | −0.39 | 6 | 2 |  |  |
| 7.5 | 10 |  | 73.85 | −0.531 | 6 | 1 |  |  |

*Q2Dx3;5,12,19 Paclitaxel injected one hour after Compound (xvii).

TABLE 4

DOSE RESPONSE OF COMPOUND (xvii) WITH AND WITHOUT
PACLITAXEL AGAINST THE PC-3 IN VIVO TUMOR MODEL.
PC-3#8

DRUGS

| Compound (xvii) (IV) Dose (mg/kg) | Paclitaxel (IP) Dose (mg/kg) | % Toxic Death | MTW d35 % T/C | Net Log Cell Kill | Total # Animals | REGRESSIONS PARTIAL | REGRESSIONS COMPLETE | REGRESSIONS CURE |
|---|---|---|---|---|---|---|---|---|
| 0 | 30 | 17 | 2 | toxic | 6 | 5 |  |  |
| 0 | 20 | 0 | 2.86 | 1.98 | 6 | 5 | 1 |  |
| 0 | 10 | 0 | 55.12 | −0.672 | 6 | 2 |  |  |
| 30 | 0 | 33 | 0.09 | 0.967 | 6 | 3 | 1 |  |
| 30 | 30 | 33 | 0.09 | 0.603 | 6 | 4 |  |  |
| 30 | 20 | 0 | 0.09 | 1.07 | 6 | 4 |  | 2 |
| 30 | 10 | 17 | 0.09 | 1.98 | 6 | 3 | 2 |  |

*Q2Dx3;5,12,19 Paclitaxel injected one hour after Compound (xvii).

The following compounds were prepared and can be prepared according to the Examples:
3. Xaa Val Xab Pro Xac
4. Xaa Val Xab Pro Xad 5. Xaa Val Xab Pro Xae
6. Xaa Val Xab Pro Xaf
7. Xaa Val Xab Pro Xag
8. Xaa Val Xab Pro Xah
9. Xaa Val Xab Pro Xai
10. Xaa Val Xab Pro Xak
11. Xaa Val Xab Pro Xal
12. Xaa Val Xab Pro Xam
13. Xaa Val Xab Pro Xan
14. Xaa Val Xab Pro Xao
15. Xaa Val Xab Pro Xap
16. Xaa Val Xab Pro Xaq
17. Xaa Val Xab Pro Xar
18. Xaa Val Xab Pro Xas
19. Xaa Val Xab Pro Xat
20. Xaa Val Xab Pro Xau
21. Xaa Val Xab Pro Xav
22. Xaa Val Xab Pro Xaw
23. Xaa Val Xab Pro Xax
24. Xaa Val Xab Pro Xay
25. Xaa Val Xab Pro Xaz
26. Xaa Val Xab Pro Xba
27. Xaa Val Xab Pro xbb
28. Xaa Val Xbc Pro Xay
29. Xaa Val Xab Pro Xbd
30. Xaa Val Xab Pro Xbe
31. Xaa Val Xab Pro Xbf
32. Xaa Val Xab Pro Xba
33. Xaa Val Xab Pro Xbh
34. Xaa Val Xab Pro Xbi
35. Xaa Val Xab Pro Xbk
36. Xaa Val Xab Pro Xbl
37. Xaa Val Xab Pro Xbm
38. Xaa Val Xab Pro Xbn
39. Xaa Val Xab Pro Xbo
40. Xaa Val Xab Pro Xbp
41. Xaa Val Xab Pro Xbq
42. Xaa Val Xab Pro Xbr
43. Xaa Val Xab Pro Xbs
44. Xaa Val Xab Pro Xbt
45. Xaa Val Xab Pro Xbu
46. Xaa Val Xab Pro Xbv
47. Xaa Val Xab Pro Xbw
48. Xaa Val Xab Pro Xbx
49. Xaa Val Xab Pro Xby
50. Xaa Val Xab Pro Xbz
51. Xaa Val Xab Pro Xca
52. Xaa Val Xab Pro Xcb
53. Xaa Val Xab Pro Xcc
54. Xaa Val Xab Pro Xcd
55. Xaa Val Xab Pro Xce
56. Xaa Val Xab Pro Xcf
57. Xaa Xdf Xab Pro Xay
58. Xaa Val Xab Pro Xch
59. Xaa Val Xab Pro Xci
60. Xaa Val Xab Pro Xck
61. Xaa Val Xab Pro Xcl
62. Xaa Val Xab Pro Xcm
63. Xaa Val Xab Pro Xcn
64. Xaa Val Xab Pro Xco
65. Xaa Val Xab Pro Xcp
66. Xaa Val Xab Pro Xcq
67. Xaa Val Xab Pro Xer
68. Xaa Val Xab Pro Xcs
69. Xaa Val Xab Pro Xct
70. Xaa Val Xab Pro Xcu
71. Xcw Val Xab Pro Xcv
72. Xcx Val Xab Pro Xcv
73. Xaa Val Xab Pro Pro Xcy
74. Xaa Val Xab Pro Pro Xcz
75. Xaa Val Xda Pro Xcv
76. Xaa Xdb Xab Pro Xcv
77. Xdc Val Xab Pro Xcv
78. Xaa Ile Xab Pro Xcv
79. Xdd Val Xab Pro Xcv
80. Xde Val Xab Pro Xcv
81. Xaa Xdf Xab Pro Xcv
82. Xaa Val Xab Pro Xcg
83. Xaa Val Xab Pro Pro Xdg
84. Xaa Val Xab Pro Pro Xdh
85. Xaa Val Xab Pro Pro Xdi
86. Xaa Val Xab Pro Pro Xdk
87. Xaa Val Xdl Pro Xcv
88. Xde Val Xab Pro Xay
89. Xaa Val Xdl Pro Xay
90. Xaa Val Xab Pro Xdm
91. Xaa Val Xab Pro Xdn
92. Xaa Val Xab Pro Xdo
93. Xaa Val Xab Pro Xdp
94. Xaa Val Xab Pro Xdq
95. Xaa Val Xab Pro Pro Xdr
96. Xaa Val Xab Pro Xds
97. Xaa Val Xbc Pro Xcv
98. Xaa Ile Xab Pro Xay
99. Xcw Val Xab Pro Xay
100. Xaa Val Xbc Pro Xal
101. Xaa Val Xdl Pro Xal
102. Xaa Xdf Xab Pro Xal
103. Xaa Ile Xab Pro Xal
104. Xdd Val Xab Pro Xal
105. Xde Val Xab Pro Xal
106. Xcx Val Xab Pro Xcy
107. Xcw Val Xab Pro Xal
108. Xcx Val Xab Pro Xal
109. Xcw Val Xab Pro Xav
110. Xcx Val Xab Pro Xav
111. Xcw Val Xab Pro Xaw
112. Xcx Val Xab Pro Xaw
113. Xab Val Xab Pro Xay
114. Xab Val Xab Pro Xcv
115. Xab Val Xab Pro Xal
116. Xab Val Xab Pro Xam
117. Xab Val Xab Pro Xan
118. Xab Val Xab Pro Xao
119. Xab Val Xab Pro Xav
120. Xab Val Xab Pro Xaw
121. Xab Val Xab Pro Xat
122. Xab Val Xab Pro Xau
123. Xab Val Xab Pro Xbf
124. Xab Val Xab Pro Xbm
125. Xab Val Xab Pro Xbn
126. Xab Val Xab Pro Xbo
127. Xab Val Xab Pro Xch
128. Xaa Val Xab Pro Xdt
129. Xaa Val Xab Pro Xdu
130. Xaa Val Xab Pro Xdv
131. Xaa Val Xab Pro Xdw
132. Xaa Val Xab Pro Xdx
133. Xaa Val Xab Pro Xdy
134. Xaa Val Xab Pro Xdz
135. Xaa Val Xab Pro Xea
136. Xaa Val Xab Pro Xeb
137. Xaa Val Xab Pro Xec
138. Xaa Val Xab Pro Xed 139. Xaa Val Xab Pro Xef
140. Xaa Val Xab Pro Xeg
141. Xaa Val Xab Pro Xeh
142. Xaa Val Xab Pro Xei
143. Xaa Val Xab Pro Xek
144. Xaa Val Xab Pro Xel
145. Xaa Val Xab Pro Xem
146. Xaa Val Xab Pro Xen
147. Xaa Val Xab Pro Xeo
148. Xaa Val Xab Pro Xep
149. Xaa Val Xab Pro Xeq
150. Xaa Val Xab Pro Xer
151. Xaa Val Xab Pro Xcq
152. Xaa Val Xab Pro Pro Val Phe
153. Xaa Val Xab Pro Xet Val Phe $NH_2$
154. Xaa Val Xer Pro Pro Val Phe $NH_2$
155. Xaa Val Xbc Pro Pro Val Phe $NH_2$
156. Xaa Ile Xab Pro Pro Val Phe $NH_2$
157. Xaa Leu Xab Pro Pro Val Phe $NH_2$
158. Xde Val Xab Pro Pro Val Phe $NH_2$
159. Xdd Val Xab Pro Pro Val Phe $NH_2$
160. Xes Val Xab Pro Pro Val Phe $NH_2$
161. Xeu Val Xab Pro Pro Val Phe $NH_2$
162. Xaa Val Xab Pro Pro Phe Phe $NH_2$
163. Xaa Val Xab Pro Pro Val $NH_2$
164. Xaa Val Xab Pro Xev
165. Xaa Val Xab Pro Pro $NH_2$
166. Xaa Val Xab Pro Pro
167. Xaa Val Xab Pro Xew
168. Xaa Val Xab Xex
169. Xdd Val Xab Pro Pro $NH_2$
170. Xaa Xdf Xab Pro Pro $NH_2$
171. Xaa Val Xab Pro Xey
172. Xaa Val Xab Pro Xez
173. Xfa Val Xab Pro Pro Val Phe $NH_2$
174. Xaa Val Xab Pro Pro Xfb
175. Xaa Val Xab Pro Xfc
176. Xaa Val Xab Pro Xfd
177. Xaa Val Xab Pro Xfe
178. Xaa Val Xab Pro Xff
179. Xaa Val Xab Pro Xfg
180. Xaa Val Xab Pro Xfh
181. Xaa Val Xab Pro Xfi
182. Xaa Val Xab Pro Xfj
183. Xaa Val Xdl Pro Pro $NH_2$
184. Xaa Val Xfk Pro Pro $NH_2$
185. Xaa Val Xfl Pro Xfh
186. Xaa Val Xfk Pro Xfh
187. Xcx Val Xab Pro Xfh
188. Xaa Val Xab Pro Pro Xdf Phe $NH_2$
189. Xaa Val Xab Pro Pro Leu Phe $NH_2$
190. Xaa Val Xab Pro Pro Ile Phe $NH_2$

TABLE 5

SEQUENCE IDENTIFICATION OF COMPOUNDS PREPARED ACCORDING TO THE EXAMPLES AND CONTAINED IN THE FIGURE

| Compound Number(s) | SEQ ID NO: |
|---|---|
| 2A, 3–56, 58–72, 75, 77, 79–80, 82, 87–94, 96–97, 99–101, 104–151, 164, 167, 171–172, 175–182, 185–187, and Compounds i–xvii of the Figure | 1 |
| 57 | 2 |
| 73–74, 83–86, 95, 174 | 3 |
| 76, 81, 102 | 4 |
| 78, 98, 103 | 5 |
| 1A, 152, 154–155, 158–161, 173 | 6 |

TABLE 5-continued

SEQUENCE IDENTIFICATION OF COMPOUNDS PREPARED ACCORDING TO THE EXAMPLES AND CONTAINED IN THE FIGURE

| Compound Number(s) | SEQ ID NO: |
|---|---|
| 153 | 7 |
| 156 | 8 |
| 157 | 9 |
| 162 | 10 |
| 163 | 11 |
| 1B, 2B, 165–166, 169, 183 | 12 |
| 168 | 13 |
| 170 | 14 |
| 188 | 15 |
| 189 | 16 |
| 190 | 17 |

Examples for the MS-characterization of the synthesized novel compounds are listed below:

| EXAMPLE | Fast atom bombardment MS analysis |
|---|---|
| 3. | 565 |
| 4. | 579 |
| 5. | 593 |
| 6. | 607 |
| 7. | 621 |
| 8. | 635 |
| 11. | 607 |
| 12. | 607 |
| 13. | 621 |
| 14. | 649 |
| 15. | 635 |
| 16. | 635 |
| 17. | 635 |
| 18. | 635 |
| 19. | 621 |
| 20. | 621 |
| 21. | 635 |
| 22. | 635 |
| 25. | 633 |
| 26. | 647 |
| 27. | 661 |
| 31. | 623 |
| 32. | 671 |
| 33. | 667 |
| 34. | 681 |
| 35. | 655 |
| 36. | 655 |
| 37. | 669 |
| 38. | 621 |
| 39. | 635 |
| 41. | 649 |
| 42. | 621 |
| 43. | 633 |
| 44. | 667 |
| 45. | 607 |
| 46. | 647 |
| 47. | 668 |
| 48. | 655 |
| 49. | 669 |
| 50. | 685 |
| 51. | 629 |
| 52. | 625 |
| 53. | 721 |
| 55. | 579 |
| 58. | 623 |
| 61. | 597 |
| 62. | 621 |
| 63. | 609 |
| 64. | 625 |
| 65. | 635 |
| 66. | 591 |
| 67. | 715 |

-continued
| EXAMPLE | Fast atom bombardment MS analysis |
|---|---|
| 68. | 685 |
| 69. | 685 |
| 70. | 591 |
| 71. | 607 |
| 72. | 621 |
| 74. | 706 |
| 75. | 579 |
| 76. | 579 |
| 77. | 579 |
| 78. | 607 |
| 79. | 607 |
| 80. | 607 |
| 81. | 607 |
| 82. | 637 |
| 83. | 692 |
| 84. | 706 |
| 85. | 706 |
| 86. | 706 |
| 87. | 607 |
| 90. | 635 |
| 92. | 659 |
| 93. | 617 |
| 94. | 636 |
| 95. | 678 |
| 128. | 671 |
| 131. | 625 |
| 139. | 625 |
| 151. | 637 |
| 152. | 798 |
| 153. | 810 |
| 154. | 812 |
| 155. | 812 |
| 156. | 812 |
| 157. | 812 |
| 258. | 812 |
| 159. | 811 |
| 160. | 825 |
| 161. | 881 |
| 162. | 845 |
| 163. | 649 |
| 164. | 737 |
| 165. | 550 |
| 166. | 551 |
| 167. | 731 |
| 168. | 550 |
| 169. | 566 |
| 170. | 566 |
| 171. | 635 |
| 172. | 704 |
| 173. | 853 |
| 174. | 740 |
| 175. | 619 |
| 176. | 845 |
| 177. | 649 |
| 178. | 691 |
| 179. | 717 |
| 180. | 641 |
| 181. | 579 |
| 182. | 595 |
| 183. | 566 |
| 184. | 566 |
| 185. | 669 |
| 186. | 656 |
| 187. | 669 |
| 188. | 811 |
| 189. | 812 |
| 190. | 812 |
The symbols used in the description of the compounds of Formula I have the following meanings:
| Xaa: | N,N-Dimethylvaline |
|---|---|
| Xab: | N-Methylvaline |
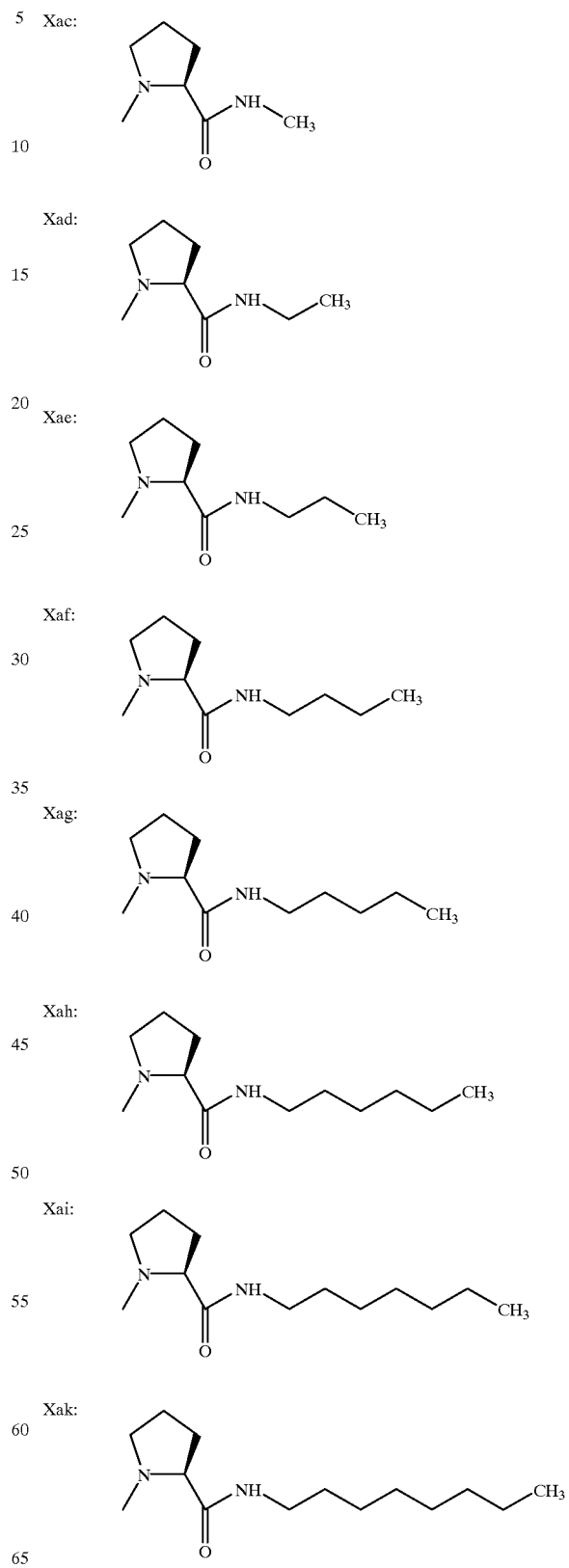

Xal: 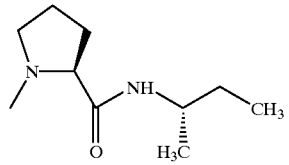
Xam: 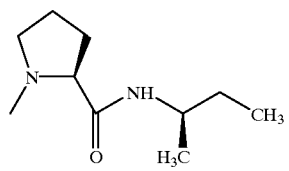
Xan: 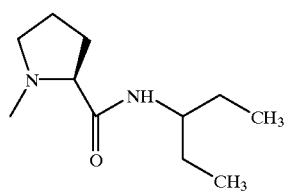
Xao: 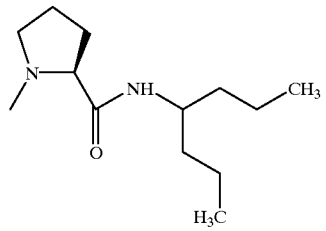
Xap: 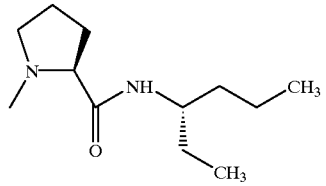
Xaq: 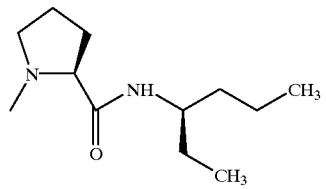
Xar: 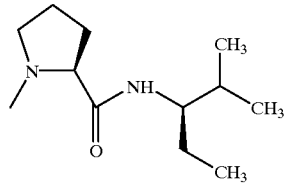
Xas: 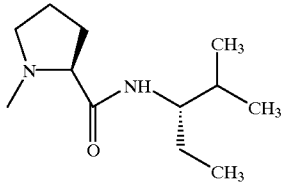
Xat: 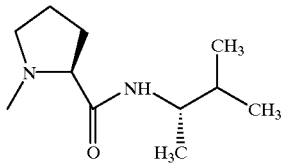
Xau: 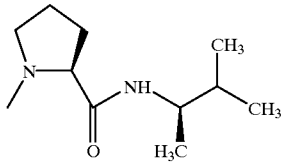
Xav: 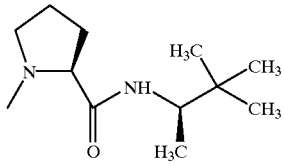
Xaw: 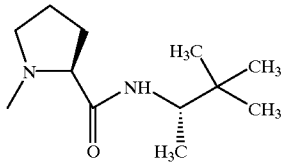
Xax: 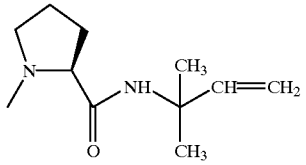
Xay: 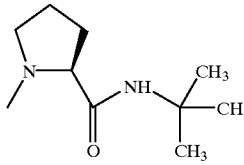
Xaz: 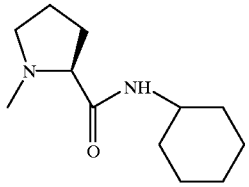

-continued
Xba: 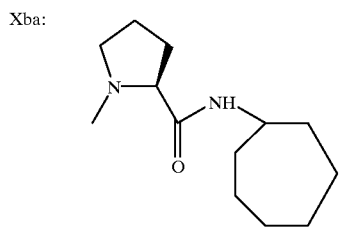
Xbb: 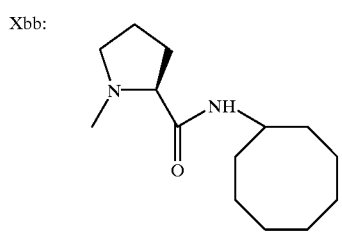
Xbc: N-Methyl-isoleucine
Xbd: 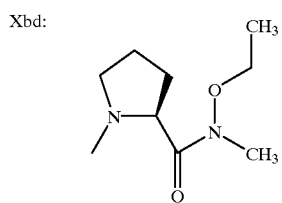
Xbe: 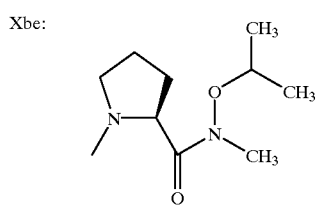
Xbf: 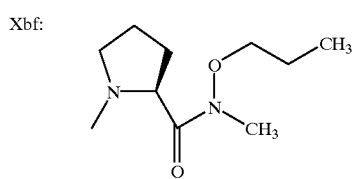
Xbg: 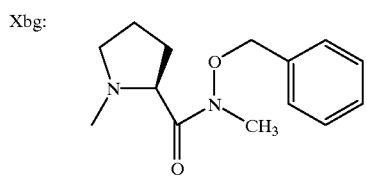
Xbh: 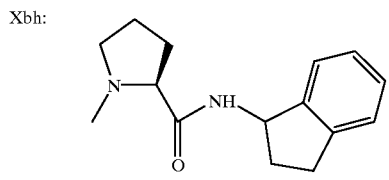
-continued
Xbi: 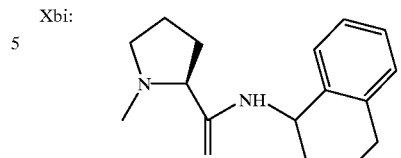
Xbk: 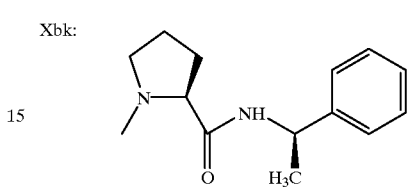
Xbl: 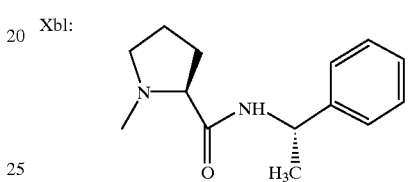
Xbm: 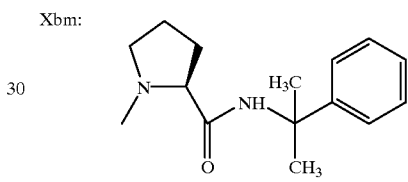
Xbn: 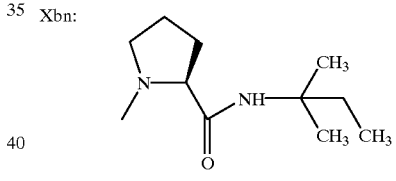
Xbo: 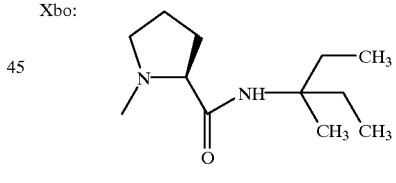
Xbp: 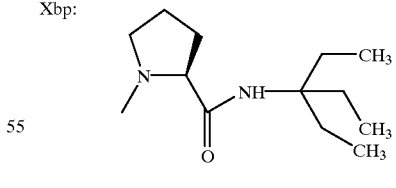
Xbq: 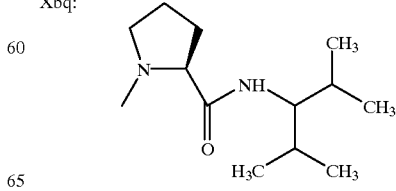

-continued
Xbr: 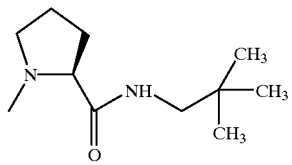
Xbs: 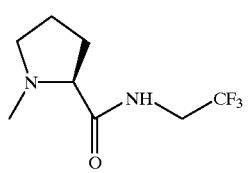
Xbt: 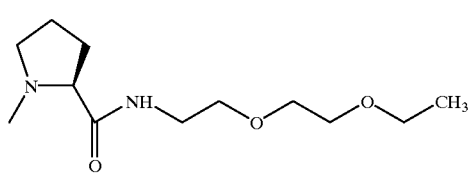
Xbu: 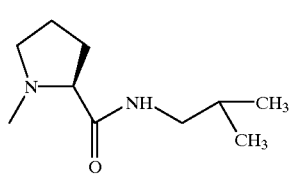
Xbv: 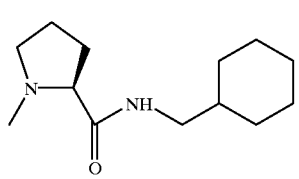
Xbw 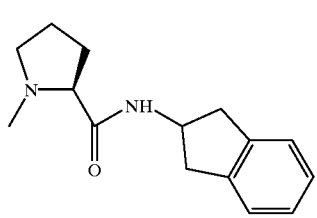
Xbx: 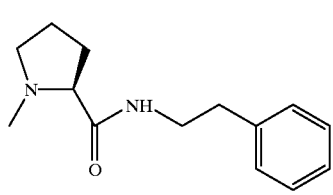
Xby: 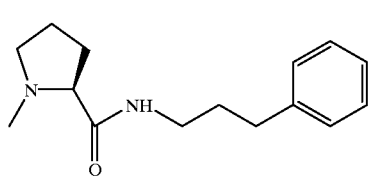
-continued
Xbz: 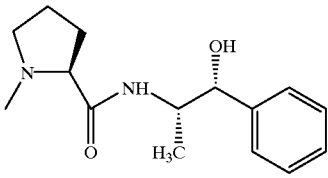
Xca: 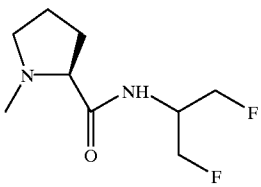
Xcb: 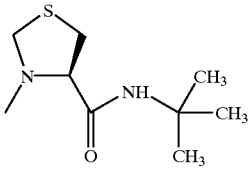
Xcc: Proline adamantyl (1)amide
Xcd: 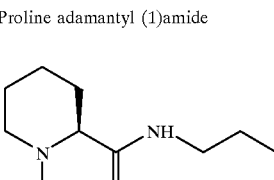
Xce: 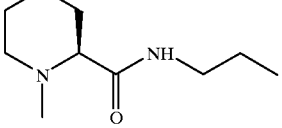
Xcf: 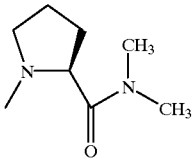
Xcg: 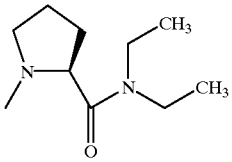
Xch: 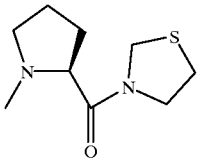

-continued
Xci: 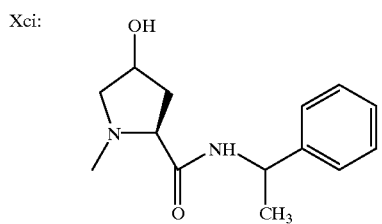
Xck: 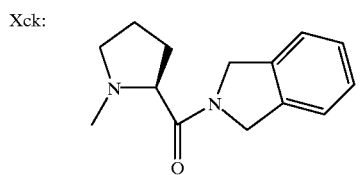
Xcl: 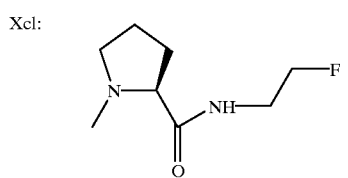
Xcm: 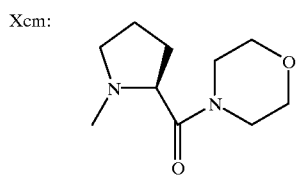
Xcn: 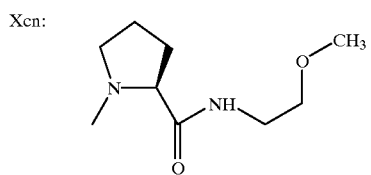
Xco: 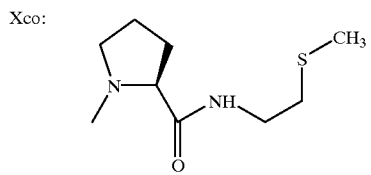
Xcp: 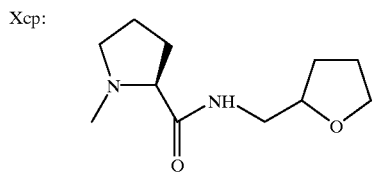
Xcq: 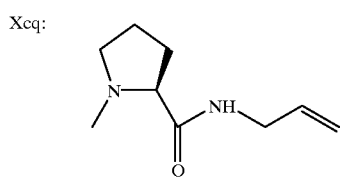
-continued
Xcr: 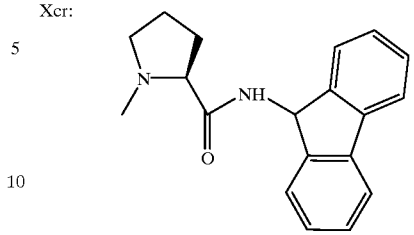
Xcs: 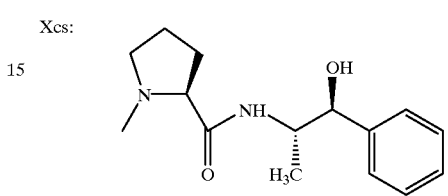
Xct: 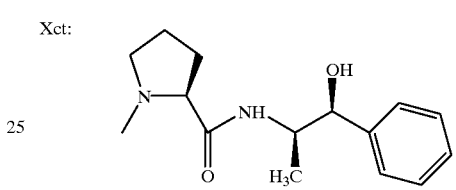
Xcu: 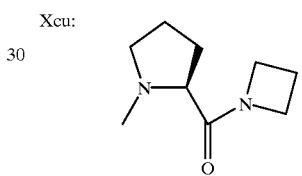
Xcv: 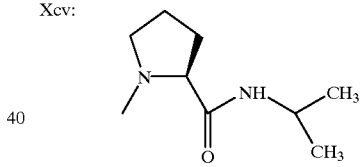
Xcw: N-Methyl-N-ethyl-valine
Xcx: N,N-Diethylvaline
Xcy: 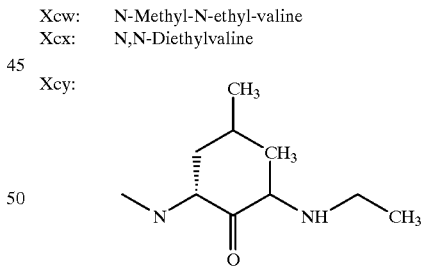
Xcz: 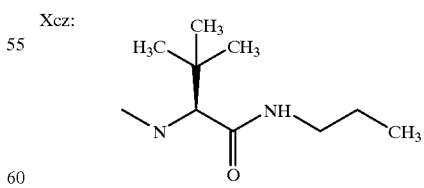
Xda: N-Methyl-2-aminobutyroyl
Xdb: 2-aminobutyroyl
Xdc: N,N-Dimethyl-2-aminobutyroyl
Xdd: N,N-Dimethyl-2-tert.butylglycine
Xde: N,N-Dimethyl-isoleucine
Xdf: 2-tert.butylglycine -continued
Xdg: 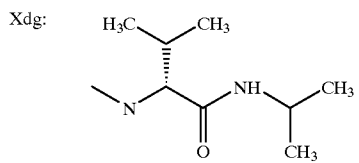
Xdh: 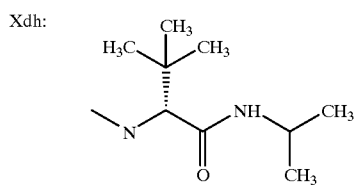
Xdi: 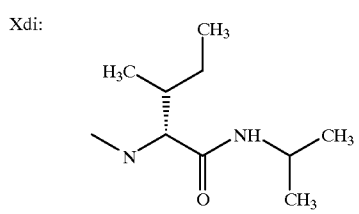
Xdk: 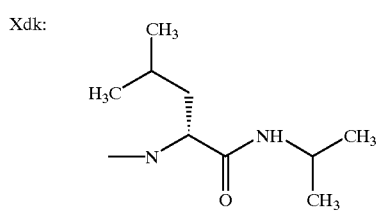
Xdl: N-Methyl-2-tert.butylglycine
Xdm: 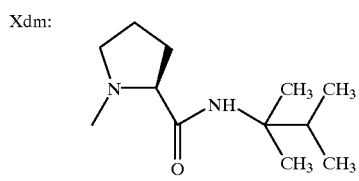
Xdn: 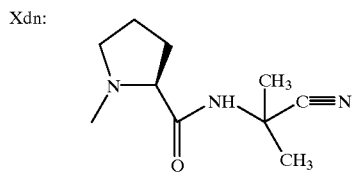
Xdo: 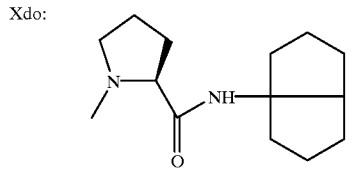
Xdp: 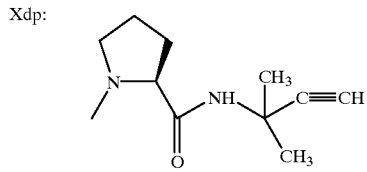
-continued
Xdq: 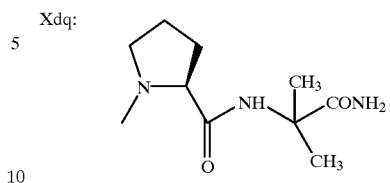
Xdr: 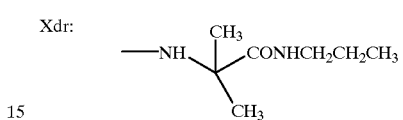
Xds: 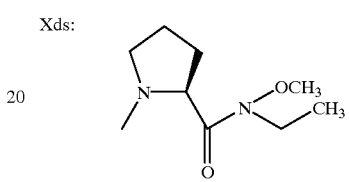
Xdt: 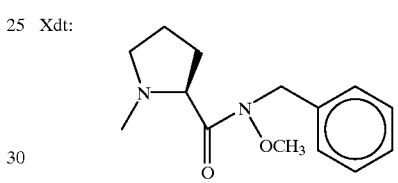
Xdu: 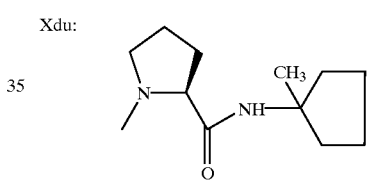
Xdv: 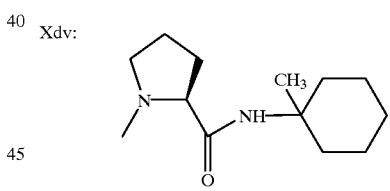
Xdw: 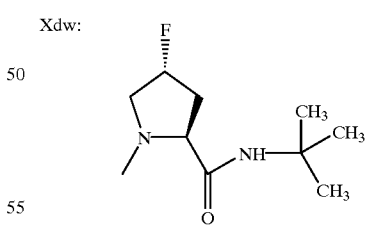
Xdx: 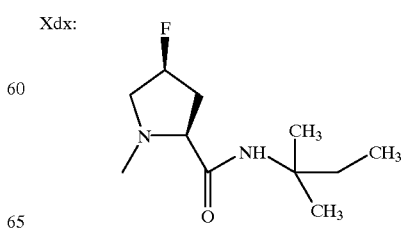

Xdy: 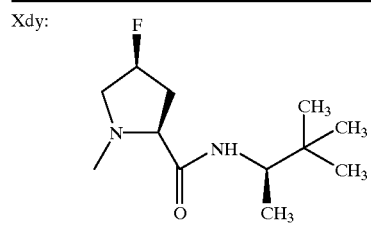
Xdz: 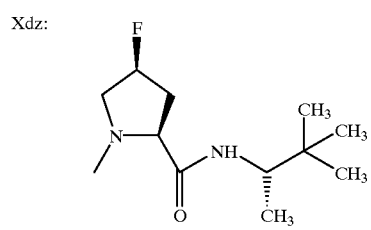
Xea: 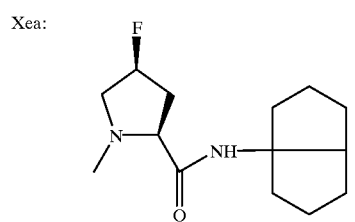
Xeb: 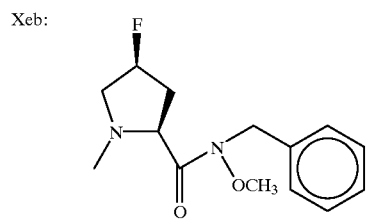
Xec: 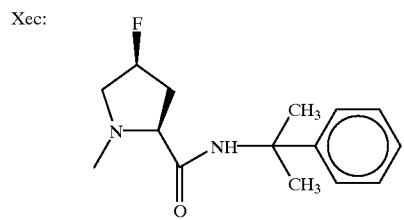
Xed: 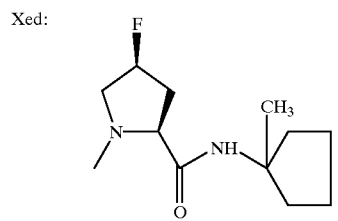
Xee: 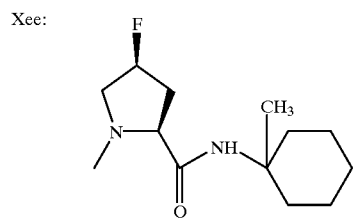
Xef: 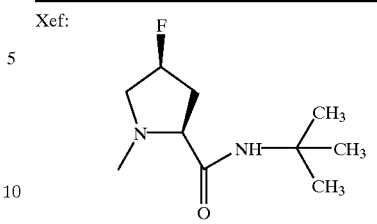
Xeg: 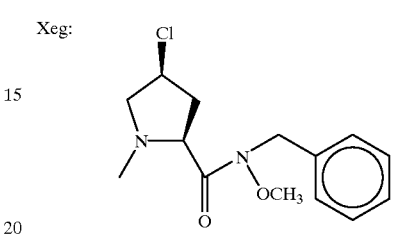
Xeh: 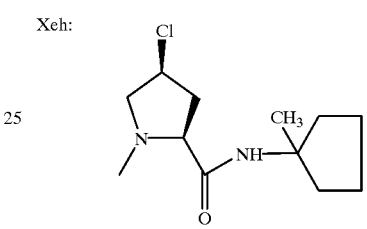
Xei: 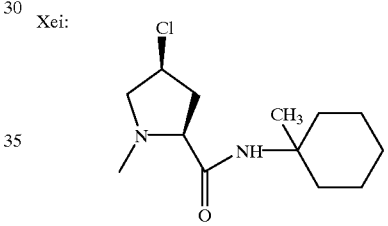
Xek: 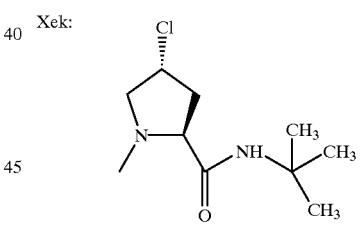
Xel: 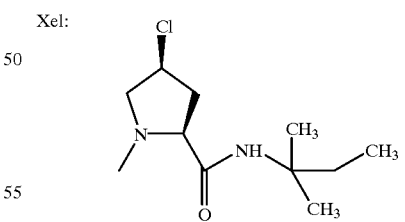
Xem: 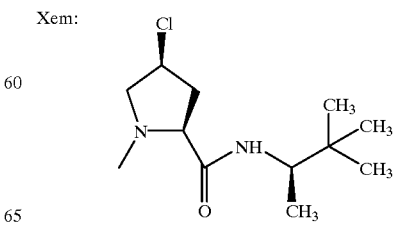

-continued
Xen: 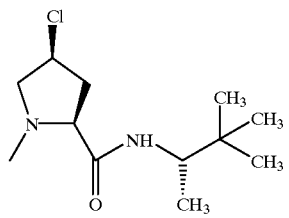
Xeo: 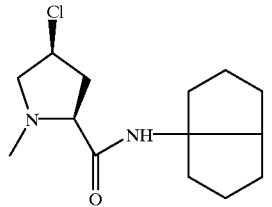
Xep: 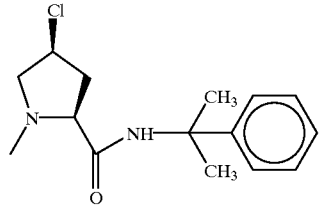
Xeq: 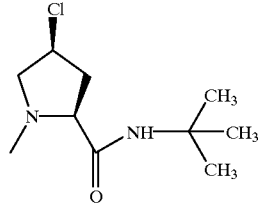
Xer: N-Methylleucine
Xes: N-Acetyl-N-methylvaline
Xet: pipecolinic acid
Xeu: N,N-Dibutylvaline
Xev: 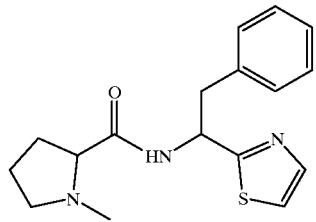
Xew: 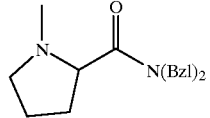
Xex: 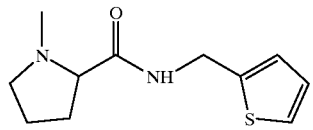
-continued
Xey: 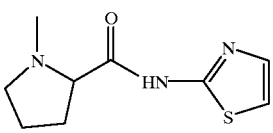
Xez: 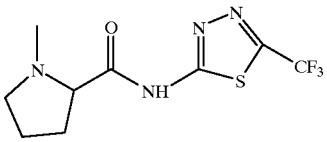
Xfa: N,N-dipropylvaline
Xfb: 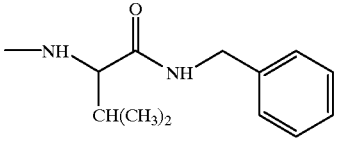
Xfc: 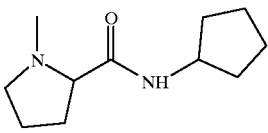
Xfd: 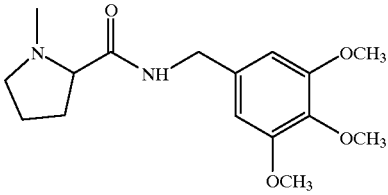
Xfe: 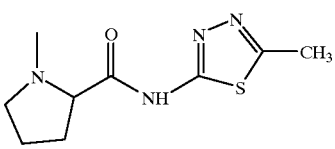
Xff: 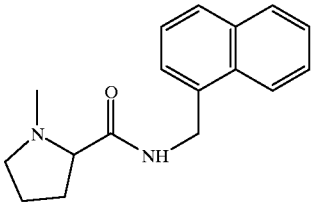
Xfg: 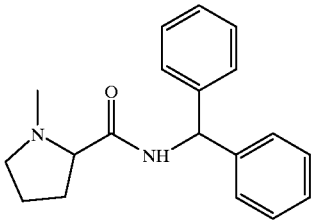

Xfh: 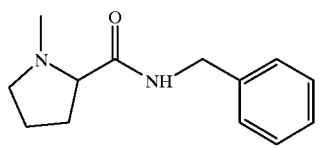

Xfi: 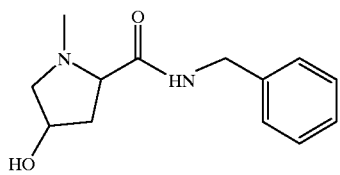

Xfj: 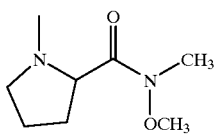

Xfk: N-Ethylvaline
Xfl: N-Methyl-3-tert-butylalanine

Equivalents

Those skilled in the art will recognize or be able to ascertain using no more than routine experimentation many equivalents to the specific embodiments of the invention described herein. Such equivalents are intended to be encompassed in the scope of the following claims.

What is claimed is:

1. A pharmaceutical composition comprising:
an effective amount of a first compound selected from the group consisting of paclitaxel and taxotere; and
an enhanced effective amount of a second compound, wherein the second compound is of Formula I $$R^1 R^2 N-CHX-CO-A-B-D-(E)_s-(F)_t-(G)_u-K \quad (I)$$

wherein:

$R^1$ is alkyl, cycloalkyl, alkylsulfonyl, fluoroalkyl, or aminosulfonyl;

$R^2$ is hydrogen, alkyl, fluoroalkyl or cycloalkyl;

$R^1$—N—R together may be a pyrrolidino or piperidino residue;

A is a valyl, isoleucyl, leucyl, allo-isoleucyl, 2,2-dimethylglycyl, 2-cyclopropylglycyl, 2-cyclopentylglycyl, 3-tert-butylalanyl, 2-tert -butylglycyl, 3-cyclohexylalanyl, 2-ethylglycyl, 2-cyclohexylglycyl, norleucyl or norvalyl residue;

B is a N-alkyl-valyl, -norvalyl, -leucyl, -isoleucyl, -2-tert-butylglycyl, -3-tert -butylalanyl, -2-ethylglycyl, -2-cyclopropylglycyl, -2-cyclopentylglycyl, -norleucyl or -2-cyclohexylglycyl residue;

D is a prolyl, homoprolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;

E is a prolyl, homoprolyl, hydroxyprolyl, 3,4-dehydroprolyl, 4-fluoroprolyl, 3-methylprolyl, 4-methyl prolyl, 5-methylprolyl, azetidine-2-carbonyl, 3,3-dimethylprolyl, 4,4-difluoroprolyl, oxazolidine-4-carbonyl or thiazolidine-4-carbonyl residue;

F and G are independently selected from the group consisting of prolyl, homoprolyl, hydroxyprolyl, thiazolidinyl-4—carbonyl, 1-aminopentyl-1-carbonyl, valyl, 2-tert-butylglycyl, isoleucyl, leucyl, 3-cyclohexylalanyl, phenylalanyl, N-methylphenylalanyl, tetrahydrosioquinclyl-2-histidyl, 1-aminoindyl-1-carbonyl, 3-pyridylalanyl, 2-cyclohexylglycyl, norleucyl, norvalyl, neopentylglycyl, trytophanyl, glycyl, 2,2-dimethylglycyl, alanyl, β-alanyl and 3-naphthylalanyl residues;

X is hydrogen, alkyl, cycloalkyl, —$CH_2$—cyclohexyl or arylalkyl;

s, t and u are independently 0 or 1; and

K is hydroxy, alkoxy, phenoxy, benzyloxy or an amino moiety of the formula $R^5$—N—$R^6$ wherein: $R^5$ is hydrogen; hydroxy; $C_{1-7}$ alkoxy; benzyloxy; phenyloxy; fluorine substituted or unsubstituted $C_{1-7}$-linear or branched alkyl; $C_{1-12}$ linear or branched hydroxyalkyl; $C_{3-10}$-cycloalkyl; unsubstituted benzyl; or mono-, di or tri-substituted benzyl, wherein the substituents are independently selected from the group consisting of: $CF_3$, nitro, $C_{1-7}$ alkylsulfonyl, $C_{1-14}$ alkoxy, phenoxy, benzoxy, halogen, $C_{1-4}$-alkyl, cyano, hydroxy, $N(CH_3)_2$, COOMe, COOEt, COOiPr, and $COONH_2$;

$R^6$ is hydrogen; fluorine substituted unsubstituted $C_{1-12}$ linear or branched alkyl; $C_{1-12}$ linear or branched hydroxyalkyl; $C_{3-10}$-cycloalkyl; $(CH_2)_v$ -$C_{3-7}$-cycloalkyl (v=0,1,2, or 3); norephedryl; norpseudoephedryl; quinolyl; pyrazyl; —$CH_2$-benzimidazolyl; (1)-adamantyl; (2)-adamantyl; —$CH_2$-adamantyl; alpha -methyl-benzyl; alpha-dimethylbenzyl; —$(CH_2)_v$-phenyl (v=0,1,2, or 3) wherein the phenyl group is unsubstituted or mono- or di-substituted and the substituents are independently selected from the group consisting of: $CF_3$, nitro, $C_{1-7}$ alkylsulfonyl, $C_{1-4}$ alkoxy, phenoxy, benzoxy, halogen, $C_{1-4}$-alkyl or fused alkyl, cyano, hydroxy, $N(CH_3)_2$, COOMe, COOEt, COOiPr, and $COONH_2$; —$(CH_2)_m$-naphthyl (m=0 or 1) —$(CH_2)_w$-benzhydryl (w=0,1, or 2); biphenyl; picolyl; benzothiazolyl; benzoisothiazolyl; benzopyrazolyl; benzoxazolyl; —$(CH_2)_m$-fluorenyl (m=0 or 1); pyrimidyl; —$(CH_2)_m$-indanyl (m=0 or 1); —$(CH_2CH_2O)_y$—$CH_3$ (y=0,1,2,3,4, or 5); —$(CH_2CH_2O)_y$—$CH_2CH_3$ (y=0,1,2,3,4, or 5) NH-phenyl wherein the phenyl group is unsubstituted or mono- or di-substituted and the substituents are independently selected from the group consisting of: $CF_3$, nitro, $C_{1-7}$ alkylsulfonyl, $C_{1-4}$ alkoxy, halogen, $C_{1-4}$ alkyl or fused alkyl, cyano, hydroxy, COOMe, COOEt, COOiPr, and $COONH_2$; —$NCH_3$—$C_6H_5$; —NH—$CH_2$—$C_6H_5$; —$NCH_3$—$CH_2$—$C_6H_5$; 5-membered unsubstituted or mono- or di-substituted heteroaryl wherein the substituted selected from the group consisting of: $CF_3$, nitro, thiomethyl, thioethyl, $C_{3-6}$-cycloalkyl, —$CH_2$—COOEt, $C_{3-4}$-alkylene group forming a bicyclic system with the heterocycle; phenyl; —$CHR^7$-5-membered heteroaryl selected from the group consisting of: $CF_3$, nitro, cyano, halogen, COOMe, COOEt, COOiPr, $CONH_2$, $C_{1-4}$-alkyl, $C_{1-4}$-alkoxy, phenyl, benzyl, naphthyl, and $C_{1-7}$-alkylsulfonyl; $R^7$ is hydrogen, linear or branched $C_{1-5}$ alkyl, and benzyl; or $R^7$ and $R^5$ together form a group —$(CH_2)_3$— or —$(CH_2)_4$—;

and the salts thereof with physiologically tolerated acids.

2. The pharmaceutical composition of claim 1 further comprising a pharmaceutically acceptable carrier.

3. A composition of claim 1 wherein for the compound of Formula I $R^1$ and $R^2$ are each methyl or ethyl; X is isopropyl, sec-butyl or tert-butyl; s is 1; t and u are each 0; A is valyl, 2-ethylglycyl, isoleucyl or 2-tert -butylglycyl; B is N-methylvalyl, -2-ethylglycyl, -1-isoleucyl or -2-tertbutylglycyl; D is prolyl, 4-fluoroprolyl, thiazolidinyl-4-carbonyl, or 3,4-dehydroprolyl; E is prolyl, 4-fluoroprolyl, thiazolidinyl -4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$–$C_4$ alkoxy and $R^6$ is a $C_1$–$C_{12}$ linear or branched alkyl group selected from the group of monovalent radicals consisting of;

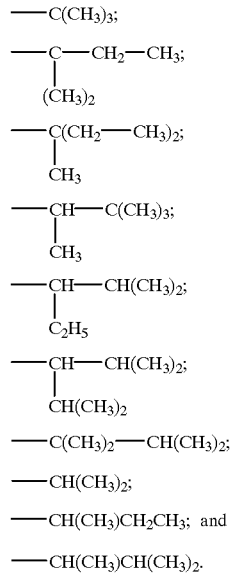

4. A composition of claim 3 wherein the monovalent radical is —$C(CH_3)_3$.

5. A composition of claim 1 wherein for the compound of Formula I $R^1$ and $R^2$ are each methyl or ethyl; X is isopropyl, sec-butyl or tert-butyl; s is 1; t and u are each 0; A is valyl, 2-ethylglycyl, isoleucyl or 2-tert -butylglycyl; B is N-methylvalyl, -2-ethylglycyl, -1-isoleucyl or -2-tertbutylglycyl; D is prolyl, 4-fluoroprolyl, thiazolidinyl-4-carbonyl, or 3,4-dehydroprolyl; E is prolyl, 4-fluoroprolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$–$C_4$ alkoxy and $R^6$ is selected from the group of monovalent radicals consisting of: (CH₂)v-phenyl (wherein v is 1) and α,α-dimethylbenzyl.

6. A composition of claim 1 wherein for the compound of Formula I R¹ and R² are each methyl or ethyl; X is isopropyl, sec-butyl or tert-butyl; s is 1; t and u are each 0; A is valyl, 2-ethylglycyl, isoleucyl or 2-tert -butylglycyl; s is N-methylvalyl, -2-ethylglycyl, 1-isoleucyl or 2-2tertbutylglycyl; D is prolyl, 4-fluoroprolyl, thiazolidinyl-4-carbonyl, or 3,4-dehydroprolyl; 1E is prolyl, 4-fluoroprolyl, thiazolidinyl-4-carbonyl, homoprolyl, 3,4-dehydroprolyl or hydroxyprolyl; and K is a substituted amino moiety having the formula R⁵—N—R⁶ wherein R⁵ is hydrogen or C₁–C₄ alkoxy and R⁶ is a C₁–C₁₂ linear or branched hydroxyalkyl.

7. A composition of claim 6 wherein R⁶ is 3-hydroxy-1, 1-dimethylpropyl.

8. A composition of claim 1 wherein for the compound of Formula I R¹ and R² are each methyl or ethyl; X is isopropyl, sec-butyl or tert-butyl; s is 1; t and u are each 0; A is valyl 2-etlhylglycyl, isoleucyl or 2-tert -butylglycyl; B is N-methylvalyl, -2-ethylglycyl, -1-isoleucyl or -2-tertbutylglycyl; D is prolyl, 4-fluoroprolyl, thiazolidinyl-4-carbonyl, or 3,4-dehydroprolyl; E is prolyl, 4-fluoroprolyl, thiazolidinyl-4-carbonyl, homoprolyl, 3,4-dehydroprolyl or hydroxyprolyl; and K is a substituted amino moiety having the formula R⁵—N—R⁶ wherein R is hydrogen or C₁–C₄ alkoxy and R⁶ is a C₃₋₁₀ cycloalkyl selected from the group consisting of: (1) -adamantyl, (2)-adamantyl, cyclobutyl, cyclopentyl, cyclohexyl, 1-methylcyclopentyl, 1-methylcyclohexyl and octa-1-yl.

9. A composition of claim 1 wherein for the compound of Formula I R¹ and R² are each methyl; X is isopropyl; s is 1; t and u are each 0; A is valyl; B is N-methylvalyl; D is prolyl; E is prolyl; R⁵ is benzyl and R⁶ is hydrogen.

10. A composition of claim 1 wherein the first compound is paclitaxel and wherein for the second compound of Formula I, R¹ and R² are each methyl; X is isopropyl; s is 1; t and u are each 0; A is valyl; B is N-methylvalyl; D is prolyl; E is prolyl; R⁵ is benzyl and R⁶ is hydrogen.

11. A composition of claim 1 wherein for the compound of Formula I R¹ and R² are each methyl or ethyl; X is isopropyl, sec-butyl or tert-butyl; s is 1; t arid u are each 0; A is valyl, isoleucyl, 2-ethylglycyl, or 2-tertbutylglycyl; B is N-methylvalyl, -1-isoleucyl, 2-ethylglycyl or -2-tertbutylglycyl; D is prolyl, 4-fluoroprolyl, thiazolidinyl-4-carbonyl, or 3,4-dehydroprolyl; and E is prolyl, 3-methylprolyl, 4-fluoroprolyl, thiazolidinyl-4-carbonyl, homoprolyl, 3,4-dehydroprolyl or hydroxyprolyl.

12. A method for treating cancer in a mammal, selected from the group consisting of: lung, breast, colon, prostate, bladder, rectal, endometrial and hematological cancers, comprising:

administering tor said mammal an effective amount of a first compound selected from the group consisting of paclitaxel a taxotere; and administering to said mammal an enhanced effective amount of a second compound of Formula I:

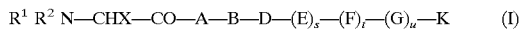
R¹ R² N—CHX—CO—A—B—D—(E)ₛ—(F)ₜ—(G)ᵤ—K    (I)

wherein:

R¹ is alkyl, cycloalkyl, alkylsulfonyl, fluoroalkyl, or aminosulfonyl;

R² is hydrogen, alkyl, fluoroalkyl or cycloalkyl;

R¹—N—R² together may be a pyrrolidino or piperidino residue;

A is a valyl, isoleucyl, leucyl, allo-isoleucyl, 2,2-dimethylglycyl, 2-cyclopropylglycyl, 2-cyclopentylglycyl, 3-tert-butylalanyl, 2-tert -butylglycyl, 3-cyclohexylalanyl, 2-ethylglycyl, 2-cyclohexylglycyl, norleucyl or norvalyl residue;

B is a N-alkyl-valyl, -norvalyl, -leucyl, -isoleucyl, -2-tert-butylglycyl, -3-tert -butylalanyl, -2-ethylglycyl, -2-cyclopropylglycyl, -2-cyclopentylglycyl, -norleucyl or -2-cyclohexylglycyl residue;

D is a prolyl, homoprolyl, hydroxyprolyl, 3,4-dehydroprolyl, 4-fluoroprolyl, 3-methylprolyl, 4-methylprolyl, 5-methylprolyl, azetidine-2-carbonyl, 3,3-dimethylprolyl, 4,4-difluoroprolyl, oxazolidine-4-carbonyl or thiazolidine-4-carbonyl residue;

E is a prolyl, homoprolyl, hydroxyprolyl, 3,4-dehydroprolyl, 4-fluoroprolyl, 3-methylprolyl, 4-methyl prolyl, 5-methylprolyl, azetidine-2-carbonyl, 3,3-dimethylprolyl, 4,4-difluoroprolyl, oxazolidine-4-carbonyl or thiazolidine-4-carbonyl residue;

F and G are independently selected from the group consisting ot prolyl, homoprolyl, hydroxyprolyl, thiazolidinyl-4-carbonyl, 1-aminopentyl-i-carbonyl, valyl, 2-tert -butylglycyl, isoleucyl, leucyl, 3cyclohexylalanyl, phenylalanyl, N-methylphenylalanyl, tetrahydrosioquinclyl-2-histidyl, 1-aminoindyl-1-carbonyl, 3-pyridylalanyl, 2-cyclohexylglycyl, norleucyl, norvalyl, neopentylglycyl, trytophanyl, glycyl, 2,2-dimethylglycyl, alanyl, β-alanyl and 3-naphthylalanyl residues;

X is hydrogen, alkyl, cycloalkyl, —CH₂-cyclohexyl or arylalkyl;

s, t and u are independently 0 or 1; and

K is hydroxy, alkoxy, phenoxy, benzyloxy or an amino moiety of the formula R⁵—N—R⁶ wherein:

R⁵ is hydrogen; hydroxy; C₁₋₇ alkoxyl; benzyloxy; phenyloxy; fluorine branched alkyl; C₁₋₁₂ linear or branched hydroxyalkyl; C₃₋₁₀-cycloalkyl; unsubstituted benzyl; or mono-, di- or tri-substituted benzyl, wherein the substituents are independently selected from the group consisting of: CF₃, nitro, C₁₋₇ alkylsulfonyl, C₁₋₄ alkoxy, phenoxy, benzoxy, halogen, C₁₋₄-alkyl, cyano, hydroxy, N(CH₃)₂, COOMe, COOEt, COOiPr, and COONH₂;

R⁶ is hydrogen; fluorine substituted or unsubstituted C₁₋₁₂ linear or branched alkyl; C₁₋₁₂ linear or branched hydroxyalkyl; C₃₋₁₀-cycloalkyl; —(CH₂)ᵥ—C₃₋₇-cycloalkyl (v=0,1,2, or 3); norephedryl; norpseudoephedryl; quinolyl; pyrazyl; —CH₂—benzimidazolyl; (1) -adamantly; (2) -adamantyl; —CH₂-adamantyl; alpha -methyl-benzyl; alpha-dimethylbenzyl; —(CH₂)ᵥ-phenyl (v=0,1,2, or 3) wherein the phenyl group is unsubstituted or mono- or di-substituted and alkylsulfonyl, C₁₋₄ alkoxy, phenoxy, benzoxy, halogen, C₁₋₄-alkyl or fused alkyl, cyano, hydroxy, N(CH₃)₂, COOMe, COOEt, COOiPr, and COONH₂; —(CH₂)ₘ-naphthyl (m=0 or 1); —(CH₂)w-benzhydryl (w=0,1, or 2); biphenyl; picolyl; benzothiazolyl; benzoisothiazolyl; benzopyrazolyl; benzoxazolyl; —(CH₂)ₘ-fluorenyl (m=0 or 1); pyrimidyl; —(CH₂)ₘ-indanyl (m=0 or 1); —(CH₂CH₂O)ᵧ—CH₃ (y=0,1,2,3,4, or 5); —(CH₂CH₂O)ᵧ-CH₃ (y=0,1,2,3,4, or 5) NH-phenyl wherein the phenyl group is unsubstituted or mono- or di-substituted and the substituents are independently selected from the group consisting of: CF₃, nitro, C₁₋₇ alkylsulfonyl, C₁₋₄ alkoxy, halogen, C₁₋₄ alkyl or fused alkyl, cyano, hydroxy, COOMe, COOEt, COOiPr, and COONH₂; —NCH₃—CH₂—

$C_6H_5$; —NH—$CH_2$—$C_6H_5$; —$NCH_3$—$CH_2$—$CH_5$; 5-membered unsubstituted or mono- or di-substituted heteroaryl wherein the substituents are selected from the group consisting of: $CF_3$, nitro, thiomethyl, thioethyl, $C_{3-6}$-cycloalkyl, —$CH_2$—COOEt, $C_{3-4}$-alkylene group forming a bicyclic system with the heterocycle; phenyl; —$CHR^7$-5-membered heteroaryl wherein the heteroaryl group consisting of: $CF_3$, nitro, cyano, halogen, COOMe, COOEt, COOiPr, $CONH_2$, $C_{1-4}$-alkyl, $C_{1-4}$-alkoxy, phenyl, benzyl, naphthyl, and $C_{1-7}$-alkylsulfonyl; $R^7$ hydrogen, linear or branched $C_{1-5}$ alkyl, and benzyl; or $R^7$ and $R^5$ together form a group —$(CH)_3$— or —$(CH_2)_1$—;
and the salts thereof with physiologically tolerated acids.

13. A method of claim 12 wherein the compound of Formula I is administered first followed by administration of the first compound.

14. A method of claim 12 wherein the first compound is administered first followed by administration of the compound of Formula I.

15. A method of claim 12 wherein the first compound and the compound of Formula I are administered simultaneously.

16. A method of claim 12 wherein said mammal is human.

17. A method of claim 11 wherein for the compound ot Formula I $R^1$ and $R^2$ are each methyl or ethyl; X is isopropyl, sec-butyl or tert-butyl; s is 1; t and u are each 0; A is valyl, 2-ethylglycyl, isoleucyl or 2-tert -butylglycyl; B is, N-methylvalyl, -2-ethylglycyl, -isoleucyl or -2-tertbutylglycyl; D is prolyl, 4-fluoroprolyl, thiazolidinyl-4-carbonyl, or 3,4-dehydroprolyl; E is prolyl, 4-fluoroprolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$–$C_4$ alkoxy and $R^6$ is a $C_1$–$C_{12}$ linear or branched alkyl group selected from the group of monovalent radicals consisting of:

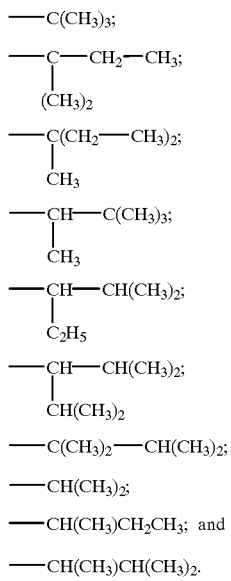

18. A method of claim 17 wherein said monovalent radical is —$C(CH_3)_3$.

19. A method of claim 11 wherein for the compound of Formula I $R^1$ and $R^2$ are each methyl or ethyl; X is isopropyl, sec-butyl or tert-butyl; s is 1; t and u are each 0; A is valyl, 2-ethylglycyl, isoleucyl or 2-tert -butylglycyl; B is N-methylvalyl, -2-ethylglycyl, -1-isoleucyl or -2-tertbutylglycyl; D is prolyl, 4-fluoroprolyl, thiazolidinyl-4-carbonyl, or 3,4-dehydroprolyl; E is prolyl, 4-fluoroprolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$–$C_4$ alkoxy ard $R^6$ is selected from the group of monovalent radicals consisting of: $(CH_2)v$-phenyl (wherein v is 1), and α,α-dimethylbenzyl.

20. A method of claim 11 wherein for the compound of Formula I $R^1$ and $R^2$ are each methyl or ethyl; X is isopropyl, sec-butyl or tert-butyl; s is 1; t arid u are each 0; A is valyl, 2-ethylglycyl, isoleucyl or 2-tert -butylglycyl; B is N-methylvalyl, -2-ethylglycyl, -1-isoleucyl or -2-tertbutylglycyl; D is prolyl, 4-fluoroprolyl, thiazolidinyl-4-carbonyl, or 3,4-dehydroprolyl; F is prolyl, 4-fluoroprolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$–$C_4$ alkoxy and $R^6$ is a $C_1$–$C_{12}$ linear or branched hydroxyalkyl.

21. A method of claim 20 wherein $R^6$ is 3-hydroxy-1,1-dimethylpropyl.

22. A method of claim 11 wherein for the compound of Formula I $R^1$ and $R^2$ are each methyl or ethyl; X is isopropyl, sec-butyl or tert-butyl; s is 1; t and u are each 0; A is valyl, 2-ethylglycyl, isoleucyl or 2-tert -butylglycyl; B is N-methylvalyl, -2-ethylglycyl, -isoleucyl or -2-tertbutylglycyl; D is prolyl, 4-fluoroprolyl, thiazolidinyl-4-carbonyl, or 3,4-dehydroprolyl; E is prolyl, 4-fluoroprolyl, thiazolidinyl-4-carbonyl, homoprolyl, 3,4-dehydroprolyl or hydroxyprolyl; and K is a substituted amino moiety having the formula $R^5$—N—$R^6$ wherein $R^5$ is hydrogen or $C_1$–$C_4$ alkoxy and $R^6$ is a $C_3$–$C_{10}$ cycloalkyl selected from the group consisting of (1)-adamantyl, (2)-adamantyl, cyclobutyl, cyclopentyl, cyclohexyl, 1-methylcyclopentyl, 1-methylcyclohexyl and octa-1-yl.

23. A method of claim 12 wherein for the compound of Formula I $R^1$ and $R^2$ are each methyl; X is isopropyl; s is 1; t and u are each 0; A is valyl; B is N-methylvalyl; D is prolyl; E is prolyl; $R^5$ is benzyl and $R^6$ is hydrogen.

24. A method of claim 12 wherein for the compound of Formula I $R^1$ and $R^2$ are each methyl; X is isopropyl; s is 1; t and u are each 0; A is valyl; B is N-methylvalyl; D is prolyl; E is prolyl; $R^5$ is benzyl and $R^6$ is hydrogen and the first compound is paclitaxel.

25. A method of claim 12 wherein for the compound of Formula I $R^1$ and $R^2$ are each methyl or ethyl; X is isopropyl, sec-butyl or tert-butyl; s is 1; t and u are each 0; A is valyl, isoleucyl, 2-ethylglycyl, or 2-tertbutylglycyl; B is N-methylvalyl, -1-isoleucyl, -2-ethylglycyl or -2-tertbutylglycyl; D is prolyl, 4-fluoroprolyl, thiazolidinyl-4-carbonyl, or 3,4-dehydroprolyl; and E is prolyl, 3-methylprolyl, 4-fluoroprolyl, thiazolidinyl-4-carbonyl, homoprolyl, 3,4-dehydroprolyl or hydroxyprolyl.

* * * * *

UNITED STATES PATENT AND TRADEMARK OFFICE
CERTIFICATE OF CORRECTION

PATENT NO. : 6,103,698
DATED : August 15, 2000
INVENTOR(S) : Teresa Barlozzari and Andreas Haupt It is certified that error appears in the above-identified patent and that said Letters Patent is hereby corrected as shown below:

| | |
|---|---|
| Column 56, claim 1, line 62, | delete "$R^1$-N-R" and insert -- $R^1$-N-$R^2$--. |
| Column 57, claim 1, line 23, | delete "tetrahydrosioquinclyl" and insert --tetrahydrosioquinolyl--. |
| Column 57, claim 1, line 40, | after $C_{1-7}$ alkylsulfonyl, delete "$C_{1-14}$" and insert --$C_{1-4}$--. |
| Column 57, claim 1, line 44, | after "substituted" insert --or--. |
| Column 57, claim 1, line 46 | delete "$(CH_2)v$" and insert -- -$(CH_2)_v$--. |
| Column 58, claim 1, line 4, | after the delete, "substituted" and insert --substituents are--. |
| Column 58, claim 1, line 9, | after "heteroaryl" insert --wherein the heteroaryl group is unsubstituted or mono- or di-substituted and the substituents are-- |
| Column 58, claim 1, line 30, | after of delete ";" and insert --:--. |
| Column 59, claim 6, line 6, | after 2-tert-butylglycyl, delete "s" and insert --B-- |
| Column 59, claim 6, line 7, | after -2-ethylglycyl, delete "1-isoleucyl" and insert -- -1-isoleucyl-- ; |

UNITED STATES PATENT AND TRADEMARK OFFICE
CERTIFICATE OF CORRECTION

PATENT NO. : 6,103,698
DATED : August 15, 2000
INVENTOR(S) : Teresa Barlozzari and Andreas Haupt It is certified that error appears in the above-identified patent and that said Letters Patent is hereby corrected as shown below:

| | |
|---|---|
| Column 59, claim 6, line 8, | delete "2-2tertbutyglycyl" and insert -- -2-tertbutylglycyl--. |
| Column 59, claim 6, line 9, | after "3,4-dehydroprolyl;" delete IE and insert --E--. |
| Column 59, claim 8, line 19, | after valyl, delete "2-etlhylglycyl," and insert -- , 2-ethylglycyl--. |
| Column 59, claim 8, line 25, | after wherein, delete "R" and insert --$R^5$--. |
| Column 59, claim 11, line 41, | after t, delete "arid" and insert --and--; |
| Column 59, claim 11, line 43, | after "-1-isoleucyl " delete 2-ethylglycyl" and insert -2-ethylglycyl--. |
| Column 59, claim 12, line 52, | after administering, delete "tor" and insert --to--. |
| Column 59, claim 12, line 54, | after paclitaxel, delete "a" and insert --and--. |
| Column 60, claim 12, line 19, | after consisting, delete "ot" and insert --of--. |
| Column 60, claim 12, line 21, | after thiazolidinyl-4-carbonyl delete "1-aminopentyl-i-carbonyl" and insert --1-aminopentyl-1-carbonyl-- |
| Column 60, claim 12, line 22, | delete "3cyclohexylanyl" and insert -- 3-cyclohexylanyl-- |

UNITED STATES PATENT AND TRADEMARK OFFICE
CERTIFICATE OF CORRECTION

PATENT NO. : 6,103,698
DATED : August 15, 2000
INVENTOR(S) : Teresa Barlozzari and Andreas Haupt It is certified that error appears in the above-identified patent and that said Letters Patent is hereby corrected as shown below:

| | |
|---|---|
| Column 60, claim 12, line 23, | delete "tetrahydrosioquinclyl" and insert --tetrahydrosioquinolyl--. |
| Column 60, claim 12, line 36, | after fluorine, insert --substituted or unsubstituted $C_{1-7}$-linear or -- |
| Column 60, claim 12, line 49, | after (1) delete "adamantly" and insert -adamantyl--. |
| Column 60, claim 12, line 53, | after "and", insert --the substitutents are independently selected from the group consisting of $CF_3$, nitro, $C_{1-7}$ --. |
| Column 60, claim 12, line 62, | after ), delete "-$(CH_2CH_2O)_y$-$CH_3$" and insert -- -$(CH_2CH_2O)_y$ -$CH_2CH_3$ --. |
| Column 61, claim 12, line 1, | after NH-$CH_2$-$C_6H_5$; delete "-$NCH_3$-$CH_2$-$CH_5$" and insert -- -$NCH_3$-$C_6H_5$ --. |
| Column 61, claim 12, line 8, | after "group" insert --is unsubstituted or mono- or di-substituted and the substituents are selected from the group --. |
| Column 61, claim 12, line 11, | after $R^7$, insert --is--. |

UNITED STATES PATENT AND TRADEMARK OFFICE
CERTIFICATE OF CORRECTION

PATENT NO. : 6,103,698
DATED : August 15, 2000
INVENTOR(S) : Teresa Barlozzari and Andreas Haupt It is certified that error appears in the above-identified patent and that said Letters Patent is hereby corrected as shown below:

| | |
|---|---|
| Column 61, claim 12, line 13, | after group, delete -(CH)$_3$- or -(CH$_2$)$_1$-, and insert -- -(CH$_2$)$_3$- or -(CH$_2$)$_4$- --. |
| Column 61, claim 17, line 25, | after claim, delete "11" and insert --12--. |
| Column 61, claim 17, line 25, | after compound, delete "ot" and insert --of--. |
| Column 61, claim 17, line 29, | after is, delete the comma. |
| Column 61, claim 17, line 13, | after alkoxzy,, delete "a" and insert --and--. |
| Column 62, claim 19, line 3, | after claim, delete "11" and insert --12--. |
| Column 62, claim 20, line 16, | after claim, delete "11" and insert --12--. |
| Column 62, claim 20, line 18, | after "t", delete arid and insert --and--. |
| Column 62, claim 20, line 22, | delete "F" and insert --E--. |

UNITED STATES PATENT AND TRADEMARK OFFICE
CERTIFICATE OF CORRECTION

PATENT NO. : 6,103,698
DATED : August 15, 2000
INVENTOR(S) : Teresa Barlozzari and Andreas Haupt It is certified that error appears in the above-identified patent and that said Letters Patent is hereby corrected as shown below:

Column 62, claim 22, line 29     after claim, delete "11" and insert --12--.

Signed and Sealed this

First Day of May, 2001

Attest:

NICHOLAS P. GODICI

Attesting Officer     Acting Director of the United States Patent and Trademark Office

UNITED STATES PATENT AND TRADEMARK OFFICE
CERTIFICATE OF CORRECTION

PATENT NO. : 6,103,698
DATED : August 15, 2000
INVENTOR(S) : Teresa Barlozzari et al.

It is certified that error appears in the above-identified patent and that said Letters Patent is hereby corrected as shown below:

Delete Drawing sheets consisting of figures 1A-1D and replace with attached figures 1A-1D.

Signed and Sealed this

Seventeenth Day of January, 2006

JON W. DUDAS
*Director of the United States Patent and Trademark Office*

(i)

(ii)

(iii)

(iv)

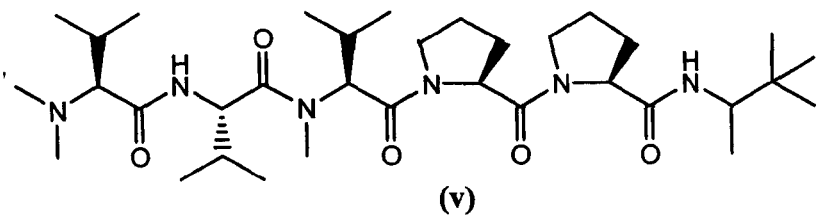
(v)
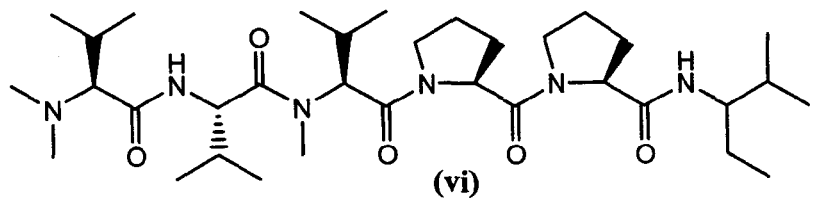
(vi)
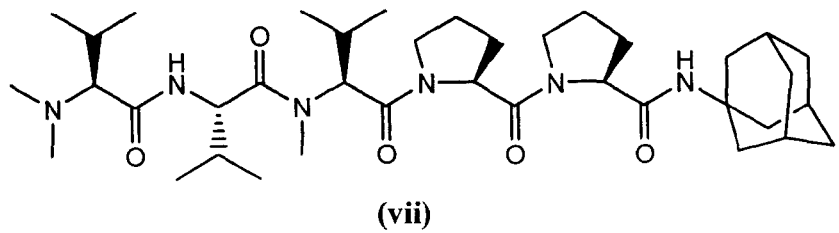
(vii)
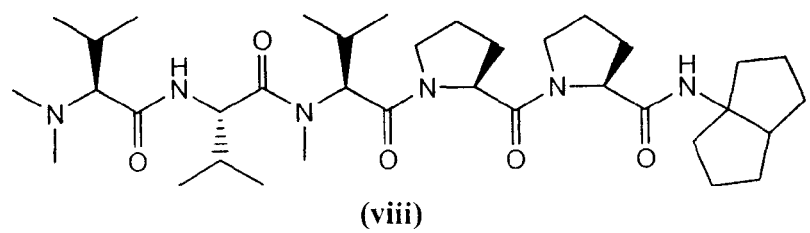
(viii)

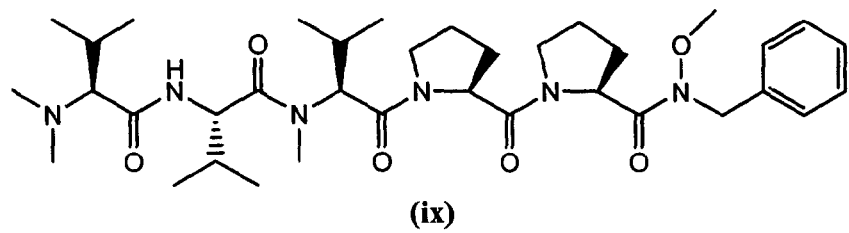
(ix)
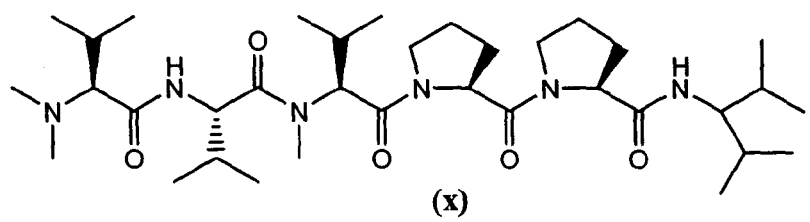
(x)
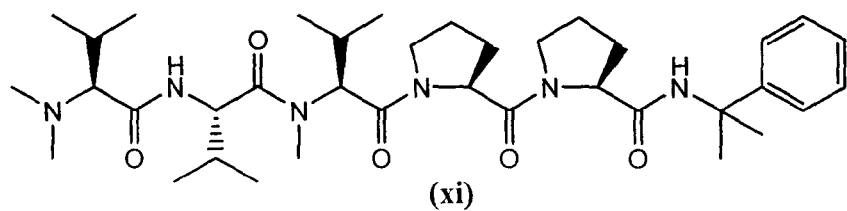
(xi)
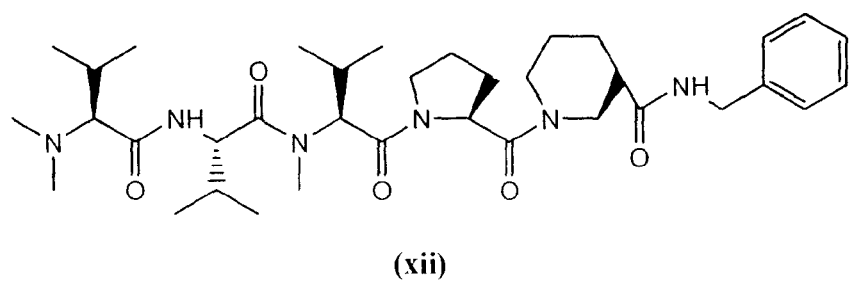
(xii)

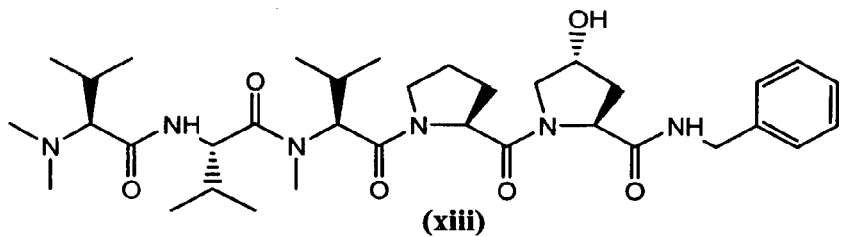
(xiii)
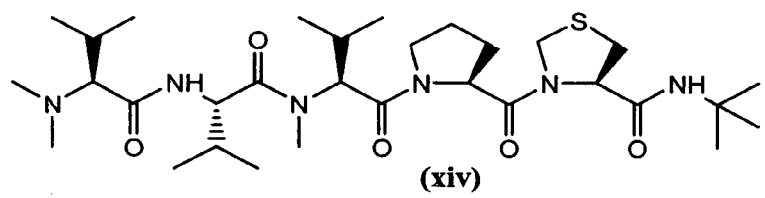
(xiv)
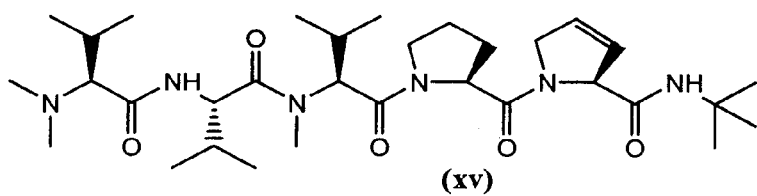
(xv)
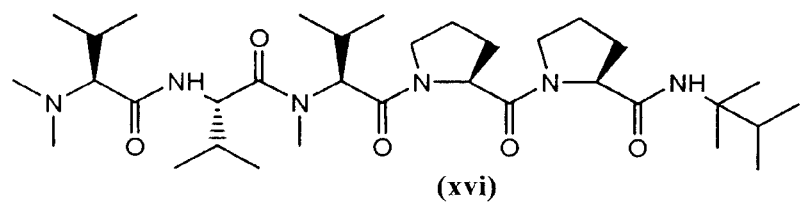
(xvi)
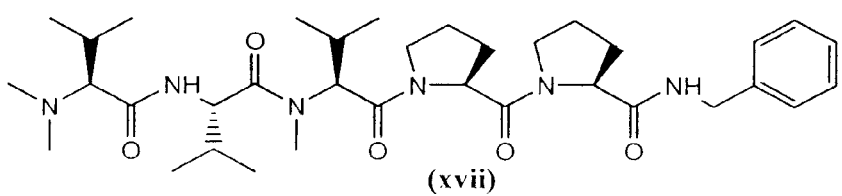
(xvii)